US000001909H

United States Statutory Invention Registration [19]

[11] Reg. Number: H1,909

Ahr

[45] Published: Nov. 7, 2000

[54] METHOD OF MAKING AN ABSORBENT COMPOSITE

[75] Inventor: Nicholas A. Ahr, Cincinnati, Ohio

[73] Assignee: The Procter & Gamble Company

[21] Appl. No.: 08/796,727

[22] Filed: Feb. 6, 1997

Related U.S. Application Data

[60] Continuation of application No. 08/470,318, Jun. 6, 1995, abandoned, which is a division of application No. 08/353, 002, Dec. 9, 1994, abandoned.

[51] Int. Cl.[7] ..... C09J 5/02

[52] U.S. Cl. ..... 156/296; 427/196; 604/368; 604/3; 162/146; 264/500

[58] Field of Search ..... 156/62.2, 273.1, 156/285, 309.9

[56] References Cited

U.S. PATENT DOCUMENTS

| | | | |
|---|---|---|---|
| 3,901,236 | 8/1975 | Assarsson et al. | 128/284 |
| 3,987,968 | 10/1976 | Moore et al. | 241/28 |
| 4,957,795 | 9/1990 | Riedel . | |
| 5,002,814 | 3/1991 | Knack et al. | 428/85 |
| 5,137,537 | 8/1992 | Herron et al. | 8/120 |
| 5,188,624 | 2/1993 | Young, Sr. et al. . | |
| 5,230,959 | 7/1993 | Young, Sr. et al. | 428/372 |
| 5,246,429 | 9/1993 | Poccia et al. | 604/368 |
| 5,259,902 | 11/1993 | Muckenfuhs . | |
| 5,300,192 | 4/1994 | Hansen et al. | 162/184 |
| 5,304,161 | 4/1994 | Noel et al. | 604/378 |
| 5,308,896 | 5/1994 | Hansen et al. | 524/13 |
| 5,352,480 | 10/1994 | Hansen et al. | 427/202 |

FOREIGN PATENT DOCUMENTS

| | | | |
|---|---|---|---|
| 0198683A2 | 10/1986 | European Pat. Off. . | |
| 0589437A1 | 3/1994 | European Pat. Off. | B32B 27/00 |

*Primary Examiner*—Charles T. Jordan
*Assistant Examiner*—Meena Chelliah

[57] ABSTRACT

Absorbent composites containing particles of absorbent gelling material and chemically stiffened, cellulosic fibers, the fibers being wrapped around and adhered to the particles, which are in individual form. The chemically stiffened, cellulosic fibers are preferably cellulosic fibers in substantially individual form having a crosslinking agent reacted with the fibers in intrafiber crosslink bond form. The absorbent composites are particularly suitable for use in the absorbent core of disposable absorbent articles such as sanitary napkins and diapers.

1 Claim, 4 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD OF MAKING AN ABSORBENT COMPOSITE

This is a continuation of application Ser. No. 08/470,318, filed on Jun. 6, 1995, now abandoned, which is a division of application Ser. No. 08/353,002, filed on Dec. 9, 1994, now abandoned.

FIELD OF THE INVENTION

The present invention relates to absorbent composites containing one or more individual particles of absorbent gelling material, the particles having chemically stiffened, cellulosic fibers wrapped around and adhered to the particles, and to methods of making the absorbent composites. The absorbent composites are especially suitable for use in the absorbent core component of disposable absorbent articles such as feminine hygiene articles and diapers.

BACKGROUND OF THE INVENTION

Absorbent gelling materials (also referred to as hydrogels, superabsorbent, or hydrocolloid materials, and hereinafter alternatively referred to as "AGM," or in the plural, "AGMs") are capable of absorbing large quantities of liquids such as water and body exudates and of retaining such absorbed liquids under moderate pressures. These absorption characteristics make them especially suitable for use in disposable absorbent articles such as diapers, sanitary napkins, incontinent devices and the like. Particulate AGMs are typically disposed in and/or on webs of absorbent fibers in the absorbent core component of such articles. For example, U.S. Pat. No. 3,699,103 issued to Harper et al. on Jun. 13, 1972 and U.S. Pat. No. 3,670,731 issued to Harmon on Jun. 20, 1972 both disclose the use of particulate AGM in absorbent articles.

Conventional particulate AGMs, however, have the limitation that the particles are not immobilized and are free to migrate during processing and/or use. Migration of the particles during processing can lead to material handling losses during manufacturing operations and, more significantly, the nonhomogeneous incorporation of the particles into structures in which the particles are being used. Nonhomogeneous incorporation of the particles can result in regions of relatively high concentration of the particulate material. When the particles are wetted, such high concentration regions tend to exhibit high resistance to liquid flow, i.e., gel blocking. Gel blocking is a particular problem where relatively high gel volume, low gel strength AGMs are used. As a result, the acquisition and/or distribution of liquids by the absorbent article is diminished, leading to inefficient utilization of the article and/or leakage.

As a result of product design or migration, the particles may be present in the vicinity of the topsheet or backsheet. The presence of the absorbent particles in these regions tends to cause a gritty feeling to the wearer, pinholing of the backsheet resulting in aesthetic negatives and/or leakage, and/or migration through the topsheet causing gel on the wearer's skin.

One approach to address the migration of particulate hydrogels in absorbent articles is disclosed in U.S. Pat. No. 3,901,236 issued to Assarsson et al. on Aug. 26, 1975. Assarsson discloses particulate hydrogels substantially coated with fibers, for example, conventional wood pulp fibers. Other composites comprising particulate absorbent materials with fibers, such as synthetic polymeric fibers or conventional wood pulp fibers, adhered thereto or embedded therein are disclosed in U.S. No. 5,230,959 issued to Young, Sr., et al. on Jul. 27, 1993 and in U.S. Pat. No. 5,002,814 issued to Knack, et al. on Mar. 26, 1991, respectively.

While some of the problems of reducing migration of particulate AGM materials have been at least partially ameliorated by previously disclosed technology, none has solved the problems in the manner or to the extent of the present invention. For example, it has been found that ordinary wood pulp fibers are less effective than the chemically stiffened, cellulosic fibers in minimizing the migration of AGM particles. In addition, the absorbent efficacy of the aforementioned materials tends to be limited as compared to the absorbent composites of the present invention. In particular, the chemically stiffened, cellulosic fibers tend to impart faster acquisition times, higher rates of fluid absorption, and higher fluid retentions to the composites, as compared to ordinary wood pulp fibers or synthetic polymeric fibers.

Thus, there is an ongoing need to minimize the migration of particulate AGMs in absorbent articles. Moreover, there is a continuing need to improve the absorbent efficacy (including fluid acquisition rates and fluid retentions) of absorbent articles incorporating particulate AGMs. It is especially desirable to provide absorbent articles of the thinnest possible configuration consistent with such absorbent efficacy.

It is therefore an object of the present invention to provide particulate, absorbent gelling materials that are relatively immobile and thus not free to migrate within or out of the absorbent cores of absorbent articles, particularly absorbent cores containing hydrophilic fibers. Another object is to provide absorbent members formed from or containing such particulate, absorbent gelling materials. Still another object of the present invention is to provide absorbent articles containing these absorbent gelling materials, which articles do not suffer from the problems of aesthetics, pin-holing, and/or gel on skin. Yet another object of the present invention is to provide absorbent articles of relatively thin configuration that meet or exceed the absorbent efficacy of absorbent articles known heretofore.

SUMMARY OF THE INVENTION

The present invention relates to absorbent composites that contain particulate AGM and chemically stiffened, cellulosic fibers, and to absorbent members and articles comprising such a composite. A composite of the present invention contains one or more AGM particles and chemically stiffened, cellulosic fibers that are wrapped around and adhered to the particles in individual form, with a substantial portion of the fiber ends protruding from the surface of the particles. The fibers can be adhered to the particles by embedment in the polymeric material of the particles, by a bonding agent, or a combination thereof. In a preferred embodiment, the fibers are adhered to the AGM particles through the use of a bonding agent.

In a preferred embodiment, the chemically stiffened, cellulosic fibers of the composite have intrafiber crosslink bonds formed by crosslinking the fibers while they are in a relatively dehydrated, defibrated (i.e., individualized), twisted, curled condition.

The absorbent composites are preferably prepared by a method that includes the step of: (1) applying a bonding agent in liquid form onto the chemically stiffened, cellulosic fibers to form treated fibers; (2) physically associating particles of polymeric, absorbent gelling material and the treated fibers while the bonding agent is in liquid form and the particles are in substantially individual form, such that the fibers wrap around the particles and the fiber ends protrude from the particles; and (3) adhering the particles and the fibers. In a preferred embodiment, the bonding agent is applied to a web containing the chemically stiffened, cellulosic fibers. According to this embodiment, the fibers that are wrapped around and adhered to a given AGM particle are mechanically substantially separated from the fibers that are wrapped around other AGM particles.

The present invention also relates to absorbent members comprising the composite. The absorbent member may consist essentially of the composite or may contain other absorbent materials. In a preferred embodiment, the absorbent member comprises the composite and an absorbent carrier means, e.g., a web of hydrophilic fibers, the composite being substantially homogeneously dispersed, more preferably homogeneously dispersed, in the absorbent carrier means.

The present invention also relates to absorbent articles, for example, feminine hygiene articles and diapers, comprising the absorbent composite. In a preferred embodiment, the absorbent article has an absorbent member that comprises the composite and an absorbent carrier means, preferably as described above.

The AGM particles of the absorbent composite tend to be immobilized by the fibrous wrap when the absorbent composite is incorporated into fibrous absorbent structures. Thus, the problems associated with migration of AGM particles are minimized. Moreover, the particles are individually cushioned by the fibers, thereby tending to reduce negative aesthetic results and pinholing, and to increase wearer comfort.

The absorbent composites of the present invention provide improved absorbent properties relative to fiber/AGM composites known heretofore. It has been found by the present inventors that the chemically stiffened, cellulosic fibers employed in the absorbent composites of the present invention provide benefits that are not achieved with ordinary wood pulp fibers or synthetic polymeric fibers.

More specifically, it has been found that the relatively stiff synthetic polymeric fibers have a higher resistance to wrapping around the AGM particles than the chemically stiffened, cellulosic fibers employed in the present invention. In addition, the synthetic fibers are cylindrically shaped while the chemically stiffened, cellulosic fibers are very thin and flat. As a result, the synthetic polymeric fibers tend to attach at various discrete spots on the AGM particles, typically at one or two spots, while the chemically stiffened, cellulosic fibers tend to conform to the shape of the AGM particle. Any point of attachment of the chemically stiffened, cellulosic fibers thus tends to have a high AGM-fiber contact surface area, relative to the synthetic polymeric fibers. As a result, a lesser number of the chemically stiffened, cellulosic fibers than the synthetic polymeric fibers is required for wrapping around the AGM particles to provide the benefits of the fiber wrap. Thus, the present invention may enable absorbent members containing relatively high AGM concentrations, which are particularly useful in thin absorbent article designs.

On the other hand, conventional wood pulp fibers are very soft and pliable relative to the chemically stiffened, cellulosic fibers employed in the present invention. Such wood pulp fibers tend to totally wrap around or conform to the AGM particles such that the fiber ends do not protrude or only protrude to a relatively minimal degree. When contacted with fluids, the fluid must first penetrate the wood pulp fiber wrap before contacting the AGM particle. Once the AGM particle is wetted, it tends to suffer from some resistance to swelling since it is constrained by the wood pulp wrap. In contrast, the chemically stiffened, cellulosic fibers conform less intimately to the shape of the AGM particle such that larger void spaces tend to be present within the fiber wrap. As a result, the chemically stiffened, cellulosic fiber wrapped AGM particles tend to have a faster fluid absorption rate and a higher fluid absorption capacity under pressure and fluid retention.

The ability of the fiber ends of the chemically stiffened, cellulosic fibers to protrude from the AGM particles tends to minimize migration of the particles in the absorbent articles incorporating the composite of the present invention, relative to composites of absorbent particles and ordinary wood pulp fibers. The protrusion also tends to increase the absorbent properties (including the fluid retention, acquisition time and absorption rate) of the absorbent articles relative to those containing composites of AGM particles and ordinary wood pulp fibers.

DETAILED DESCRIPTION OF PREFERRED EMBODIMENTS

Figure 1:
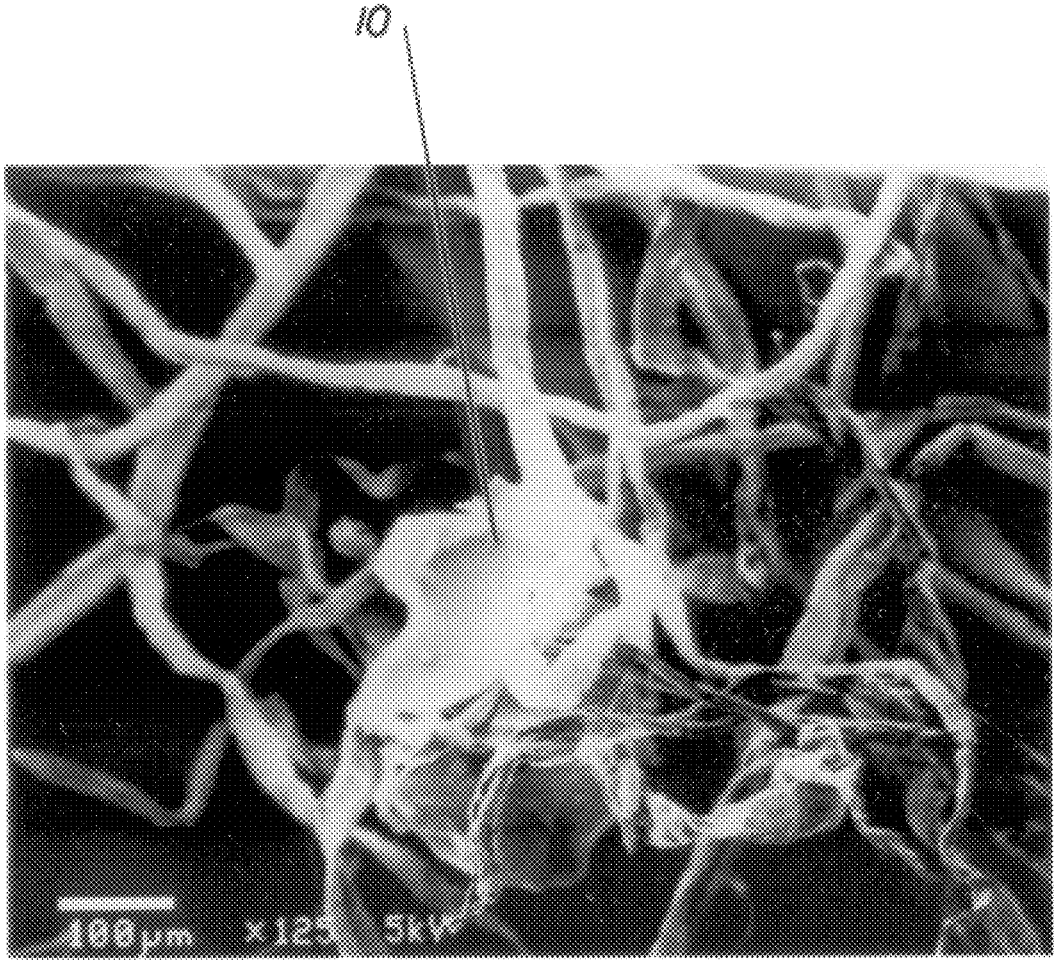
FIG. 1 is a photomicrograph of an absorbent composite according to the present invention.

The absorbent composites of the present invention contain particles of absorbent gelling material (AGM) and chemically stiffened, cellulosic fibers.

By "particles", "particulate" and the like it is meant that the absorbent gelling material is in the form of discrete units. The particles can comprise granules, pulverulents, spheres, flakes, or fibers. Thus, the particles can have any desired shape such as cubic, rod-like, polyhedral, spherical, rounded, angular, irregular, randomly-sized irregular shapes (e.g., pulverulent products of a grinding or pulverizing step) or shapes having a large greatest dimension/smallest dimension ratio like needle-like, flake-like, or fibrous shapes, and the like. Although the particles may have sizes varying over a wide range, the particle size typically ranges from about 1 micron to about 2000 microns in diameter or cross-section, and preferably ranges from about 50 microns to about 1000 microns.

Absorbent gelling materials are capable of absorbing large quantities of liquids such as water and body exudates, and of retaining such absorbed liquids under moderate pressures. Although the selection of the absorbent gelling material is not critical to the present invention, typical and preferred absorbent gelling materials are described in U.S. Pat. No. Re. 32,649, reissued to Brandt et al. on Apr. 19, 1988; U.S. Pat. 4,666,983, issued to Tsubakimoto et al. on May 19, 1987; and U.S. Pat. No. 4,625,001, issued to Tsubakimoto et al. on Nov. 25, 1986; each of these patents being incorporated herein by reference. The AGMs are typically substantially water-insoluble, absorbent, hydrogel-forming, polymeric materials. Mixtures of absorbent gelling materials may also be used.

Preferred absorbent gelling materials for use in the present invention possess a carboxyl group. These materials include hydrolyzed starch-acrylonitrile graft copolymer, partially neutralized starch-acrylonitrile graft copolymer, starch-acrylic acid graft copolymer, partially neutralized starch-acrylic acid graft copolymer, vinyl acetate-acrylic ester copolymers, saponified vinyl acetate-acrylic ester copolymers, hydrolyzed acrylonitrile or acrylamide copolymers, slightly network crosslinked products of any of the foregoing polymers, partially neutralized polyacrylic acid, and slightly network crosslinked products of partially neutralized polyacrylic acid. These polymers may be used either independently or in an admixture of two or more of the polymers. Examples of these polymer materials are disclosed in U.S. Pat. Nos. 3,661,875; 4,076,663; 4,093,776; 4,666,983; and 4,734,498. Most preferably, the absorbent gelling material is a slightly network crosslinked product of partially neutralized polyacrylic acid or a starch derivative thereof.

The absorbent gelling material is preferably prepared by aqueous solution or other solution polymerization methods, such as described in the above-referenced U.S. Pat. No. Re. 32,649. However, it is also possible to use absorbent gelling materials prepared by other methods as are well known in the art, for example, multi-phase polymerization processing techniques such as inverse emulsion polymerization or inverse suspension polymerization procedures. For example, inverse emulsion polymerization techniques are described in U.S. Pat. No. 4,340,706, issued to Obayashi et al. on Jul. 20, 1982; U.S. Pat. No. 4,506,052, issued to Fletcher et al. on Mar. 19, 1985; and U.S. Pat. No. 4,735,987; issued to Morita et al. on Apr. 15, 1988; each of these patents being incorporated herein by reference.

The particles of absorbent gelling material may optionally be surface treated. For example, U.S. Pat. No. 4,824,901, issued to Alexander et al. on Apr. 25, 1989, discloses the surface treatment of polymeric particles with a polyquaternary amine. If surface treated, the particles are preferably surface treated as described in U.S. Pat. No. 4,734,478, issued to Tsubakimoto et al. on Mar. 29, 1988, incorporated herein by reference; and in the above-referenced U.S. Pat. No. 4,666,983.

Preferred absorbent gelling materials exhibit a high absorptive capacity. Absorptive capacity refers to the capacity of a given polymer material to absorb liquids with which it comes into contact, and can vary significantly with the nature of the liquid being absorbed and with the manner in which the liquid contacts the polymer material. For purposes of this invention, Absorptive Capacity is defined in terms of the amount of Synthetic Urine absorbed by any given polymer material in terms of grams of Synthetic Urine per gram of polymer material. Preferred absorbent gelling materials of the present invention are those which have an Absorptive Capacity of at least about 20 grams, more preferably at least about 25 grams, of Synthetic Urine per gram of polymer material. Typically, the polymer materials herein have an Absorptive Capacity of from about 40 to about 70 grams of Synthetic Urine per gram of polymer material. A method for determining the Absorptive Capacity for particulate, absorbent, polymeric compositions, which can be used herein, is described in U.S. Pat. No. 5,300,565, issued to Berg et al. on Apr. 5, 1994. This patent is incorporated herein by reference.

The absorbent composite of the present invention also contains chemically stiffened, cellulosic fibers. Cellulosic fibers are well known and include, for example, digested fibers from softwood, hardwood or cotton linters, Esparto grass, bagrasse, hemp, and flax. Fibers from other lignaceous and cellulosic fiber sources may also be used herein. The absorbent composites may contain one or more types of chemically stiffened, cellulosic fibers.

As used herein, the term "chemically stiffened cellulosic fibers" means cellulosic fibers which have been stiffened by chemical means to increase stiffness of the fibers under both dry and aqueous conditions. Such means include the addition of chemical stiffening agents which, for example, coat and/or impregnate the fibers. Such means also include the stiffening of the fibers by altering the chemical structure of the fibers themselves, e.g., by cross-linking polymer chains.

For exemplary purposes, polymeric stiffening agents which can coat or impregnate cellulosic fibers include: cationic modified starch having nitrogen-containing groups (e.g., amino groups) such as those available from National Starch and Chemical Corp., Bridgewater, N.J., USA; latex, wet strength resins such as polyamide-epichlorohydrin resin (e.g., Kymene® 557H, Hercules, Inc. Wilmington, Del., USA), polyacrylamide resin (described, for example, in U.S. Pat. No. 3,556,932 issued Jan. 19, 1971 to Coscia, et al.; also, for example, the commercially available polyacrylamide marketed by American Cyanamid Co., Stanford, Conn., USA, under the tradename Parez™ 631 N.C.); urea formaldehyde and melamine formaldehyde resins, and polyethylenimine resins. A general dissertation on wet strength resins utilized in the paper art, and generally applicable herein, can be found in TAPPI monograph series No. 29., "Wet Strength in Paper and Paperboard", Technical Association of the Pulp and Paper Industry (N.Y. 1965), incorporated herein by reference.

The fibers utilized in the composites herein can also be stiffened by means of chemical reaction. For example, crosslinking agents can be applied to the fibers which, subsequent to application, are caused to chemically form intra-fiber crosslink bonds. These crosslink bonds can increase the stiffness of the fibers. Whereas the utilization of intrafiber crosslink bonds to chemically stiffen the fibers is preferred, it is not meant to exclude other types of reactions for chemical stiffening of the fibers.

Fibers stiffened by crosslink bonds in individualized (i.e., fluffed) form are disclosed, for example, in Bernardin, U.S. Pat. No. 3,224,926, issued Dec. 21, 1965; Chung, U.S. Pat. No. 3,440,135, issued Apr. 22, 1969; Chatterjee, U.S. Pat. No. 3,932,209, issued Jan. 13, 1976 and Sangenis et al., U.S. Pat. 4,035,147, issued Jul. 12, 1977. More preferred fibers are disclosed in Dean et al., U.S. Pat. No. 4,822,453, issued Apr. 18, 1989; Dean et al., U.S. Pat. No. 4,888,093, issued Dec. 19, 1989; Schoggen et al., U.S. Pat. No. 4,889,596, issued Dec. 26, 1989; Herron et al., U.S. Pat. No. 4,889,595, issued Dec. 26, 1989; Moore et al. U.S. Pat. No. 4,898,642, issued Feb. 6, 1990; Herron et al., U.S. Pat. No. 5,183,707, issued Feb. 2, 1993. All of these patents are incorporated herein by reference.

In the more preferred stiffened fibers, chemical processing includes intrafiber crosslinking with crosslinking agents while such fibers are in a relatively dehydrated, defibrated (i.e., individualized), twisted, curled condition. The effect of crosslinking while such individualized (i.e., fluffed) fibers are in this condition is to form fibers which are stiffened and which tend to retain their twisted, curled configuration during use in the absorbent articles herein. Such fibers, and processes for making them are described in the above incorporated patents.

Suitable chemical stiffening agents that can be used for such intrafiber crosslinking include monomeric crosslinking agents including, but not limited to, $C_2$–$C_8$ dialdehydes, $C_2$–$C_8$ monoaldehydes having an acid functionality, acid analogues of $C_2$–$C_8$ dialdehydes having at least one aldehyde functional group, and oligomers of any of the forementioned compounds. These compounds are capable of reacting with at least two hydroxyl groups in a single cellulose chain or on proximately located cellulose chains in a single fiber. Such crosslinking agents contemplated for use in preparing the stiffened cellulose fibers include, but are not limited to, glutaraldehyde, glyoxal, formaldehyde, and glyoxylic acid. Cellulosic fibers stiffened by such crosslinking agents and methods of making the same are described in the above-referenced and incorporated U.S. Pat. Nos. 4,888,093; 4,898,642; 4,889,595; and 4,889,596.

Most preferably, the chemical stiffening agent that is employed for intrafiber crosslinking is a polycarboxylate. Suitable polycarboxylates include $C_2$–$C_9$ polycarboxylic acids, including aliphatic and alicyclic $C_2$–$C_9$ polycarboxylic acids either olefinically saturated or unsaturated and having at least three carboxyl groups per molecule; and aliphatic and alicyclic $C_2$–$C_9$ polycarboxylic acids having two carboxyl groups per molecule and having a carbon-carbon double bond located alpha, beta to one or both of the carboxyl groups. A given carboxyl group in such $C_2$–$C_9$ polycarboxylic acid crosslinking agents is separated from a second carboxyl group by no less than two and no more than three carbon atoms. Preferred crosslinking agents of this type are citric acid; 1,2,3 butane tetracarboxylic acid; 1,2,3 propane tricarboxylic acid; oxydisuccinic acid; tartrate monosuccinic acid; tartrate disuccinic acid, or a mixture thereof. More preferably, the crosslinking agent is citric acid. The fibers crosslinked with a $C_2$–$C_9$ polycarboxylic acid will typically have between about 0.5 mole % and about 10.0 mole % crosslinking agent, calculated on a cellulose anhydroglucose molar basis, more preferably between about 1.5 mole % and about 6.0 mole % crosslinking agent, calculated on a cellulose anhydroglucose molar basis, reacted therewith in the form of intrafiber ester crosslink bonds. Cellulosic fibers stiffened by crosslinking agents of this type and methods of making the same are described in the above-referenced and incorporated U.S. Pat. Nos. 5,183,707 and 5,190,563.

The preferred stiffened fibers that are twisted and curled can be quantified by referencing both a fiber "twist count" and a fiber "curl factor". As used herein, the term "twist count" refers to the number of twist nodes present in a certain length of fiber. Twist count is utilized as a means of measuring the degree to which a fiber is rotated about its longitudinal axis. The term "twist node" refers to a substantially axial rotation of 180° about the longitudinal axis of the fiber, wherein a portion of the fiber (i.e., the "node") appears dark relative to the rest of the fiber when viewed under a microscope with transmitted light. The twist node appears dark at locations wherein the transmitted light passes through an additional fiber wall due to the aforementioned rotation. The distance between nodes corresponds to an axial rotation of 180°. The number of twist nodes in a certain length of fibers (i.e., the twist count) is directly indicative of the degree of fiber twist, which is a physical parameter of the fiber. The procedures for determining twist nodes and total twist count are described in the hereinbefore referenced U.S. Pat. No. 5,183,707.

The preferred stiffened cellulose fibers, which are formed using a $C_2$–$C_9$ polycarboxylic acid crosslinking agent, will have an average dry fiber twist count of at least about 2.5, preferably at least about 3.0 twist nodes per millimeter. Furthermore, the average wet fiber twist count of these fibers should preferably be at least about 1.5; preferably at least about 2.0, and should also preferably be at least about 1.0 twist nodes per millimeter less than the average dry fiber twist count.

In addition to being twisted, the preferred chemically stiffened, cellulosic fibers used in the composites of the present invention are also curled. Fiber curl may be described as the fractional shortening of the fiber due to kinks, twists, and/or bends in the fiber. For the purposes of this invention, fiber curl is measured in terms of a two dimensional plane. The extent of fiber curling can be quantified by referencing a fiber curl factor. The fiber curl factor, a two dimensional measurement of curl, is determined by viewing the fiber in a two dimensional plane. To determine curl factor, the projected length of the fiber as the longest dimension of a two dimensional rectangle encompassing the fiber, $L_R$, and the actual length of the fiber, $L_A$, are both measured. The fiber curl factor can then be calculated from the following equation:

$$\text{Curl Factor}=(L_A/L_R)-1$$

An image analysis method that can be utilized to measure $L_R$ and $L_A$ is described in U.S. Pat. No. 5,183,707. Preferably the chemically stiffened, cellulosic fibers utilized in the absorbent composites of the present invention will have a curl factor of at least about 0.30, and more preferably of at least about 0.50.

The degree of stiffening, dependent upon the type and amount of stiffening agent (i.e., crosslinking agent) used, the degree of dehydration of the fibers during curing of the crosslinking agent, and the curing time and conditions, affect the ability of the fiber to take up fluid and the tendency of the fiber to swell. The fiber stiffness as it relates to resistance to fiber wall swelling can be quantified by referencing the water retention value (WRV) of the stiffened cellulosic fibers used in the absorbent composites herein. WRV is a measure of the amount of water retained by a mass of fibers after substantially all of the interfiber water has been removed. Another parameter which can be used to characterize the nature of the stiffened fibers formed by crosslinking fibers in relatively dehydrated form is that of alcohol retention value (ARV). ARV is a measure of the extent to which a fluid, e.g., isopropyl alcohol, which does not induce substantial fiber swelling, is taken up by the stiffened fibers. The ARV of the stiffened fibers is directly related to the extent that the fibers were swollen with the solution of crosslinking agent during the stiffening procedure. Relatively higher ARVs mean that the fibers were generally swollen to a relatively greater extent during crosslinking. Procedures for determining WRV and ARV are described in U.S. Pat. No. 4,898,642.

The WRV for the stiffened, twisted, curled fibers used in the present invention will preferably be less than about 60%, more preferably in the range of from about 28% to about 60%, even more preferably from about 28% to about 50%. In more preferred embodiments, the WRV of the fibers can range from about 30% to 45%. Fibers having a WRV within these ranges are believed to provide an optimal balance of swelling-induced untwisting and fiber stiffness.

The stiffened cellulose fibers preferred for use herein are those which have an ARV (isopropyl alcohol) of less than about 30%. The limitation that such fibers have an ARV (isopropyl alcohol) of less than about 30% is indicative of the relatively dehydrated, unswollen state of these fibers during the stiffening process. More preferably, the ARV (isopropyl alcohol) of the fibers useful herein will be less than about 27%.

The stiffened cellulose fibers herein having the preferred twist count, curl factor, WRV and ARV characteristics hereinbefore set forth, can be prepared by internally crosslinking such fibers in relatively dehydrated form while or after such fibers are being or have been dried and defibrated (i.e., "fluffed") as described in U.S. Pat. Nos. 4,888,093; 4,898,642; 4,889,595; 4,889,596; 5,183,707; and 5,190,563. It is not, however, meant to necessarily exclude other chemically stiffened cellulosic fibers from this invention, such other fibers being described in (but not limited to) the previously incorporated U.S. Pat. Nos. 3,224,926, 3,440,135, 4,035,147, and 3,932,209.

The relative amounts of particulate absorbent gelling material and chemically stiffened fibers in the composite of the present invention ranges from about 90% to about 30% AGM and from about 10% to about 70% chemically stiffened cellulosic fibers. Preferably, the composite contains from about 70% to about 30% AGM and from about 30% to about 70% chemically stiffened cellulosic fibers. More preferably, the composite contains from about 65% to about 35% AGM and from about 35% to about 65% chemically stiffened cellulosic fibers. Each of the foregoing percentages of AGM and fibers is based on the total weight of the composite.

The absorbent composites may also contain fibers other than the chemically stiffened, cellulosic fibers. For example, the absorbent composites may contain other hydrophilic fibers such as are known in the art, including ordinary wood pulp fibers or synthetic polymeric fibers, including polyolefin mono- or multi-component fibers. The multiconstituent fibers may contain two or more different polymers. When used, such other fibers will typically be employed in amounts of up to about 50% of the total weight of fibers in the absorbent composite. Such other fibers may be adhered to the AGM particles such that the fiber ends protrude from the particles.

The chemically stiffened cellulosic fibers (and other fibers which may be present in the absorbent composite) are adhered to individual particles of the absorbent gelling material. Adhesion should be sufficient to allow the chemically stiffened, cellulosic fibers to substantially immobilize the AGM particles when incorporated into an absorbent member such as described herein. Thus, gel blocking and gel on skin is minimized or avoided. Adhesion of the fibers and AGM can be caused by a number of methods. For example, the fibers may be adhered to the AGM during the polymerization of the AGM, or by using a bonding agent. The AGM polymerization method typically results in a portion of the polymeric material of the AGM mechanically engaging a sufficient portion of any individual fiber that may be in contact with the AGM particle so as to effect adherence. Methods using a bonding agent may involve such mechanical engagement and additionally involves the mechanical and/or chemical adhesion of the AGM particles and the fibers caused by the bonding agent material.

Thus, according to one method of preparing the composite, the fibers are adhered to the AGM particles during the polymerization process for forming the AGM. As stated above, absorbent gelling materials can be formed by solution polymerization methods or by reverse phase polymerization methods. The reactants that form the AGM are in a homogeneous, continuous solution (solution polymerization) or in one phase of a multiphase, typically two-phase, solution (reverse phase polymerization). The fibers can be added to either of such solutions prior to the completion of the polymerization reaction to form the AGM. Upon polymerization of the reactants, the fibers are at least partially entrapped by the resultant polymer. In solution polymerization methods, the resultant polymeric product may be ground by methods such as are known in the art of forming AGM particles. The polymeric product is preferably dried by known methods, prior to any grinding. In reverse phase polymerization methods, the polymeric product is recovered by known methods, for example, centrifugation, filtration and/or evaporation. External forces as described below are preferably applied, during or after polymerization, to promote wrapping of the AGM particles by the embedded fibers.

In a preferred embodiment, adhesion of the fibers and AGM is achieved with the use of a bonding agent. In general, the bonding agent includes substances that can be applied in liquid form to the fibers to allow its presence on the fibers to cause attachment of the AGM and the fibers. The bonding agent must also be suitable for adhering the AGM material and the fiber material. In general, the bonding agent causes the mechanical and/or chemical adhesion of the AGM particles and the fibers. Without intending to be bound by theory, it is believed that the bonding agent predisposes the AGM to wetting. As a result, the bonding agent tends to improve the absorbent (i.e., absorption) capacity and rate of absorption of absorbent members incorporating composites according to this embodiment.

The selection of a particular bonding agent will typically depend on the chemical composition of the AGM and the fiber material and can be made by one skilled in the art with a knowledge thereof. Preferably, the bonding agent is suitable for use in applications involving human contact, for example, the disposable absorbent articles herein. Thus, the bonding agent should be non-toxic and non-irritating to humans. Mixtures of bonding agents may be used.

Several types of bonding agents are suitable for use herein. Without intending to be bound by theory, it is believed that one type of bonding agent causes the polymer material of the particles to adhere to the fibers by the action of fluid surface tension forces and/or the entanglement of polymer chains due to external softening. Bonding agents of this type include (1) hydrophilic organic solvents, typically low molecular weight alcohols, for example, methanol, ethanol, isopropanol and the like, or polyols, for example, propylene glycol, glycerol and the like; (2) water; (3) volatile hydrophobic organic compounds, for example, hexane, octane, benzene, toluene and the like; and (4) mixtures thereof. Preferred bonding agents of this type are hydrophilic organic solvents, water, and a mixture thereof. These bonding agents particularly tend to predispose the AGM to wetting, such that they tend to improve the absorbent capacity and rate of absorption of the composites. More preferably, bonding agents of this type are selected from water, glycerol, propylene glycol, and mixtures thereof.

Other bonding agents tend to rely less or not at all on the fluid surface tension forces and/or the entanglement of polymer chains of swollen AGM particles for adhesion to the fibers. This type of bonding agent typically involves mechanical and/or chemical interaction between the bonding agent, fiber, and the AGM particles. For example, the bonding agent may form bridges between the AGM and the fibers. This type of bonding agent is preferred for use herein since it tends to provide stronger attachment between the fibers and AGM. Bonding agents of this type include, for example, cationic polyacrylamides, cationic amino-epichlorohydrin adducts, and mixtures thereof. Such bonding agents are preferably employed in an aqueous mixture.

In the most preferred embodiments of the present invention, the bonding agent includes water. The presence of water in the bonding agent is particularly effective in predisposing the AGM to wetting. The bonding agent preferably contains at least about 60% water, by weight of the bonding agent, with the balance consisting essentially of at least one non-aqueous bonding agent. Non-aqueous bonding agents include the aforementioned hydrophilic organic solvents, volatile hydrophobic compounds, cationic polyacrylamides, and cationic amino-epichlorohydrin adducts. The bonding agent more preferably contains from about 80% to about 90% water and from about 20% to about 10% of at least one non-aqueous bonding agent, based on the total weight of the bonding agent.

Cationic polyacrylamides are well known in the art. For example, cationic polyacrylamides that are suitable for use in the present invention are described in *Pulp and Paper; Chemistry and Chemical Technology,* 3rd. Ed., Vol. III, edited by James P. Casey, pp. 1458–1471 (John Wiley & Sons, 1981), incorporated herein by reference. Suitable cationic polyacrylamides are commercially available from the American Cyanamid Company of Wayne, N.J., under the trade name of ACCOSTRENGTH®. For example, ACCOSTRENGTH® 410, 711, 200, 85 and 86 resins are available. These resins are described in the technical brochure number PCT-729/1-1027-4K-11/81,entitled "ACCOSTRENGTH® resins," the American Cyanamid Company, November 1981, incorporated herein by reference.

As used herein, "cationic amino-epichlorohydrin adduct" refers to the reaction product between epichlorohydrin and a monomeric or polymeric amine such that the resulting reaction product has at least two cationic functional groups. These adducts can be in the form of monomeric compounds (e.g., the reaction product of epichlorohydrin and ethylene diamine), or can be in polymeric form (e.g., the reaction product between epichlorohydrin and polyamide-polyamines or polyethyleneimines). The polymeric versions of these cationic amino-epichlorohydrin adducts are typically referred to as "resins."

Monomeric amines that can be reacted with epichlorohydrin to form a cationic amino-epichlorohydrin include monomeric di-, tri- and higher amines having primary or secondary amino groups in their structures. Examples of useful diamines of this type include bis-2-aminoethyl ether, N,N-dimethylethylenediamine, piperazine, and ethylenediamine. Examples of useful triamines of this type include N-aminoethyl piperazine, and dialkylene triamines such as diethylenetriamine, and dipropylenetriamine. Preparation of these adducts, as well as a more complete description of the adducts themselves, can be found in U.S. Pat. No. 4,310,593 (Gross), issued Jan. 12, 1982, and in Ross et al, *J. Organic Chemistry*, Vol. 29, pp. 824–826 (1864). Both of these documents are incorporated by reference.

Polymeric amines such as polyethyleneimines can also be used as the amino compound for forming the adduct. A particularly desirable amino compound which can be reacted with epichlorohydrin to form preferred cationic polymeric adduct resins useful herein comprise certain polyamide-polyamines derived from polyalkylene polyamines and saturated $C_3$–$C_{10}$ dibasic carboxylic acids. Epichlorohydrin/polyamide-polyamine adducts of this kind are water-soluble, thermosetting cationic polymers which are well known in the art as wet strength resins for paper products.

In the preparation of polyamide-polyamines used to form this preferred class of cationic polymeric resins, a dicarboxylic acid is first reacted with a polyalkylene-polyamine, preferably in aqueous solution, under conditions such as to produce a water-soluble, long chain polyamide containing the recurring groups —$NH(C_nH_{2n}HN)_x$—CORCO— where n and x are each 2 or more and R is the $C_1$ to $C_8$ alkylene group of the dicarboxylic acid.

A variety of polyalkylene polyamines including polyethylene polyamines, polypropylene polyamines, polybutylene polyamines and so on can be employed to prepare the polyamide-polyamine, of which the polyethylene polyamines represent an economically preferred class. More specifically, preferred polyalkylene polyamines used to prepare the cationic polymeric resins herein are polyamines containing two primary amine groups and at least one secondary amine group in which the nitrogen atoms are linked together by groups of the formula —$C_nH_{2n}$— where n is a small integer greater than unity and the number of such groups in the molecule ranges from two up to about eight and preferably up to about four. The nitrogen atoms can be attached to adjacent carbon atoms in the group —$C_nH_{2n}$— or to carbon atoms further apart, but not to the same carbon atom. Also contemplated is the use of such polyamines as diethylenetriamine, triethylenetetramine, tetraethylenepentamine, dipropylenetriamine, and the like, which can be obtained in reasonably pure form. Of all the foregoing, the most preferred are the polyethylene polyamines containing from two to four ethylene groups, two primary amine groups, and from one to three secondary amine groups.

Also contemplated for use herein are polyamine precursor materials containing at least three amino groups with at least one of these groups being a tertiary amino group. Suitable polyamines of this type include methyl bis(3-aminopropyl) amine, methyl bis(2-aminoethyl)amine, N-(2-aminoethyl) piperazine, 4,7-dimethyltriethylenetetramine and the like.

The dicarboxylic acids which can be reacted with the foregoing polyamines to form the polyamide-polymine precursors of the preferred cationic polymeric resins useful herein preferably comprise the saturated aliphatic $C_3$–$C_{10}$ dicarboxylic acids. More preferred are those containing from 3 to 8 carbon atoms, such as malonic, succinic, glutaric, adipic, and so on, together with diglycolic acid. Of these, diglycolic acid and the saturated aliphatic dicarboxylic acids having from 4 to 6 carbon atoms in the molecule, namely, succinic, glutaric and adipic are most preferred. Blends of two or more of these dicarboxylic acids can also be used, as well as blends of one or more of these with higher saturated aliphatic dicarboxylic acids such as azelaic and sebacic, as long as the resulting long chain polyamide-polyamine is water-soluble or at least water-dispersible.

The polyamide-polyamine materials prepared from the foregoing polyamines and dicarboxylic acids are reacted with epichlorohydrin to form the cationic polymeric amino-epichlorohydrin resins. Preparation of such materials is described in greater detail in U.S. Pat. No. 2,926,116 (Keim), issued Feb. 23, 1960, U.S. Pat. No. 2,926,154 (Keim), issued Feb. 23, 1960, and U.S. Pat. No. 3,332,901 (Keim), issued Jul. 25, 1967, all of which are incorporated by reference.

The cationic polyamide-polyamine-epichlorohydrin resins preferred for use herein as the bonding agent are commercially marketed by Hercules Inc. under the trade name Kymene®. Especially useful are Kymene® 557H, Kymene® 557LX and Kymene® 557 Plus, which are the epichlorohydrin adducts of polyamide-polyamines which are the reaction products of diethylenetriamine and adipic acid. They are typically marketed in the form of aqueous solutions of the cationic resin material containing from about 10% to about 33% by weight of the resin active.

The dicarboxylic acid which can be reacted with the foregoing polyamines to form the polyamide-polyamine precursors of the preferred cationic polymeric resins useful herein may alternatively be unsaturated. Typically, the unsaturated dicarboxylic acids suitable for use herein will be selected from $C_4$–$C_{10}$ dicarboxylic acids. For example, the dicarboxylic acid may be selected from itaconic acid, citraconic acid, mesaconic acid, maleic acid, fumaric acid, and mixtures thereof.

The amino compound that can be reacted with epichlorohydrin to form a cationic polymeric adduct resin useful herein may alternatively comprise polyamide-polyamines derived from polyalkylene polyamines and saturated or unsaturated $C_4$–$C_{10}$ tribasic carboxylic acids. Suitable tricarboxylic acids include, for example, citric acid and aconitic acid.

Additional bonding agents suitable for use herein are described in U.S. Pat. No. 3,901,236 issued to Assarsson et al. on Aug. 26, 1975; U.S. Pat. No. 5,002,814 issued to Knack et al. on Mar. 26, 1991; and U.S. Pat. No. 5,230,959 issued to Young, Sr. et al. on Jul. 27, 1993. Each of these patents are incorporated herein by reference.

In general, the composites of the present invention that employ a bonding agent can be prepared in the following manner. The bonding agent is applied to the fibers, which fibers may or may not be individualized as described herein. The fibers which are thus treated with the bonding agent are then physically associated with the AGM particles so as to enable the chemically stiffened, cellulosic fibers to wrap around the AGM and to allow adhesion of the fibers and AGM. External forces are applied in order to ensure wrapping of the AGM by the fibers. Depending on the particular bonding agent which is selected, adhesion may occur without any additional steps, or may require an additional drying step or reaction step. The adhesion step is followed by a mechanical treatment step, if necessary, to substantially separate the fibers wrapping a given AGM particle from the fibers wrapping other AGM particles.

The chemically stiffened, cellulosic fibers are typically individualized prior to application of the bonding agent. As used herein, "individualized" means that the fibers are mechanically separated (i.e. "defibrated") such that there is a relatively low level of fiber entanglement, as compared to a bulk fiber source such as a fiber sheet or bale. This mechanical defibration can be performed by a variety of methods which are presently known in the art or which may hereafter become known. Mechanical defibration is preferably performed by a method wherein knot formation and fiber damage are minimized. One type of device which has been found to be particularly useful for defibrating the chemically stiffened fibers is the three stage fluffing device described in U.S. Pat. No. 3,987,968, issued to Moore et al. on Oct. 26, 1976, said patent being incorporated herein by reference. The fluffing device described in U.S. Pat. No. 3,987,968 subjects a fibrous material to a combination of mechanical impact, mechanical agitation, air agitation and a limited amount of air drying to create a substantially knot-free fluff. Other applicable methods for defibrating the fibers include, but are not limited to, treatment with a Waring blender and tangentially contacting the fibers with a rotating disk refiner or wire brush. Preferably, an air stream is directed toward the fibers being defibrated to aid in separating the fibers.

The bonding agent may be applied to the fibers by any method for applying solutions to materials, including coating, dumping, pouring, dropping, spraying, atomizing, condensing, or immersing the fibers. As used herein, the term "applied" means that at least a portion of the surface area of at least some of the fibers has an effective amount of the bonding agent on it to cause adherence of the fibers and the AGM. In other words, the bonding agent can be applied onto a portion of the surface, or onto the entire surface, of some or all of the fibers. Preferably, the bonding agent is coated onto the entire surface of most, preferably all, of the fibers so as to enhance the efficiency, strength, and density of the bonds between the AGM particles and the fibers. In a preferred embodiment, the bonding agent is applied to a web of the fibers.

The bonding agent is preferably applied to the fibers in an amount of from about 0.10% to about 25% of the weight of the fibers in the composite, the weight of the fibers being on a bone dry basis. More preferably, the bonding agent is used in an amount of about 10% to about 15% of the weight of the fibers in the composite, the weight of the fibers being on a bone dry basis. As used herein, "bone dry basis" means the actual weight of the fibers less the weight of any moisture or other volatiles which may be present in the fibers. For example, a 100 g sample of fibers containing 10% moisture has a fiber weight, on a bone dry basis, of 90 g.

Where the bonding agent includes water, care must be taken to avoid excessive swelling of the fibers. Excessive swelling of the fibers is evidenced by a significant loss in fiber curl. Without intending to be limited by theory, it is believed that when such swelling occurs, the fiber surfaces become relatively round as compared to a substantially flat surface in the unswollen condition. As a result, the bonding area between any individual fiber and any individual AGM particle tends to decrease as the fibers swell such that the degree of attachment is lessened. Swelling of the fibers is influenced by the amount of water that is applied to the fibers and the amount of time that the fibers are exposed to the water. Control of these conditions so as to avoid excessive fiber swelling will be readily understood by one skilled in the art. Typically, the contact time between the fibers and the aqueous bonding agent is kept to a very short time, e.g., from about a five minutes to a few seconds, by the addition of heat to dry or cure the mixture. The mixture is typically subjected to temperatures of about 100° C. to about 177° C., preferably from about 121° C. to about 177° C., for this purpose.

After applying the bonding agent onto the fibers and while the bonding agent is still in liquid form, the particles and fibers are physically associated together such that at a substantial number of the chemically stiffened, cellulosic fibers wrap around the individual particles and are able to adhere to the particles. Thus, the AGM particles and fibers are brought together and contacted in a manner which allows wrapping of the particles to occur by the fibers, and remain in contact with each other as component parts at at least the point where adherence of the fibers and AGM occurs. The physical association of the AGM particles and fibers preferably involves physically contacting the fibers and the AGM at at least a portion of the surface of the fibers having the bonding agent applied thereto.

The fibers and AGM particles are physically associated with the AGM particles being in substantially individual form. By "substantially individual form" it is meant that substantially all, preferably all, of the AGM particles are not in physical contact with another AGM particle. Thus, the AGM particles are substantially non-agglomerated or non-aggregated. Preferably, at least about 80%, more preferably at least about 90%, of the AGM particles are not in physical contact with another AGM particle.

The AGM particles and chemically stiffened, cellulosic fibers may be physically associated in a number of different ways in order to cause a substantial number of the fibers to wrap around the particles. For example, the fibers and AGM can be physically associated in the presence of external forces which function to draw the fibers around the individual AGM particles, e.g., pressure, vacuum, electrostatic, impact, or impingement forces. Thus, the particles and fibers may be physically associated by allowing the particles to rest adjacent the treated fibers, for example on a web of the treated fibers, with the addition of one or more of such external forces to draw the fibers around the individual AGM particles. External forces of pressure may be applied, for example, by a compaction (i.e., calendar) roll(s). Impact or impingement forces may be applied by mixing the treated fibers and AGM particles together. Any suitable method for mixing the treated fibers and AGM may be used. For example, the fibers and particles may be air entrained, or impeller or propeller blended.

While the AGM particles and fibers are physically associated together, the bonding agent is dried or reacted so as to cause adherence between the particles and the fibers. Depending on the chemical composition of the particular bonding agent, AGM, and fiber material that is selected, reaction of the bonding agent may involve reaction of the bonding agent itself, for example polymerization, or reaction of the bonding agent with the polymeric material of the AGM, with the fibers, or both.

Depending on the particular bonding agent being used, the drying and/or reacting may occur without any additional step or may involve thermal heating and/or irradiation (e.g., ultraviolet, gamma-, or x-radiation). The particular conditions required to dry and/or react the bonding agent will depend on the chemical composition of the particular bonding agent, AGM, and fiber material that is selected. Typically, the drying or reaction is caused by heating to a temperature of from about 100° C. to about 177° C., preferably from about 121° C. to about 177° C., for a time period of from about a few seconds to about 5 minutes.

The resultant composition including the fiber-wrapped AGM particles may require mechanical treatment to separate the fibers wrapping a given AGM particle from fibers wrapping other AGM particles (i.e., defibration) so as to obtain the absorbent composites of the present invention. Such defibration will typically be required where the fiber-wrapping of the AGM particles is caused by the application of pressure, vacuum, or electrostatic forces, for example, where a compaction roll is used to cause fiber wrapping. Where such forces have been applied, the fibers of the resultant composition are substantially uniformly entangled with other fibers in the composition so as to form a substantially homogeneous, relatively high density mass. By subjecting such a mass to mechanical treatment, the fibers wrapping a given AGM particle are substantially separated from the fibers wrapping other AGM particles to form the absorbent composites of the present invention. By "substantially separated," it is meant that there is a relatively low level of physical or chemical bonding between the fibers wrapping a given AGM particle and fibers wrapping other AGM particles. Preferably, less than about 50% of the number of fibers wrapping a given particle are bonded with the fibers wrapping other AGM particles. More preferably, less than about 25% of the number of fibers wrapping a given particle are bonded with the fibers wrapping other AGM particles. Most preferably, less than about 10% of the number of fibers wrapping a given particle are bonded with the fibers wrapping other AGM particles. The absorbent composites thus consist essentially of individual AGM particles ("cores") wrapped by the chemically stiffened, cellulosic fibers, with the degree of fiber bonding tending to be greatest in the vicinity of the particle surfaces and to diminish with increasing distance from the surface of a given particle. The absorbent composites have a lower density than the mass prior to mechanical treatment. The composites typically have a density of from about 0.02 g/cc to about 0.06 g/cc, generally about 0.05 g/cc. In addition, the tensile strength of the composite, ignoring the tensile strength of any given fiber in the composite, approaches zero.

The mechanical defibration step may be performed by a variety of methods as previously described in reference to individualizing the chemically stiffened, cellulosic fibers.

Where the treated fibers and AGM are physically associated by mixing, the need for defibration will depend on the conditions of mixing, including the concentration of the fibers and AGM in the system and the shear of mixing. In general, the higher the concentration or the lower the shear, the more likely the need for a defibration step to provide the absorbent composites as herein described.

Figure 2:
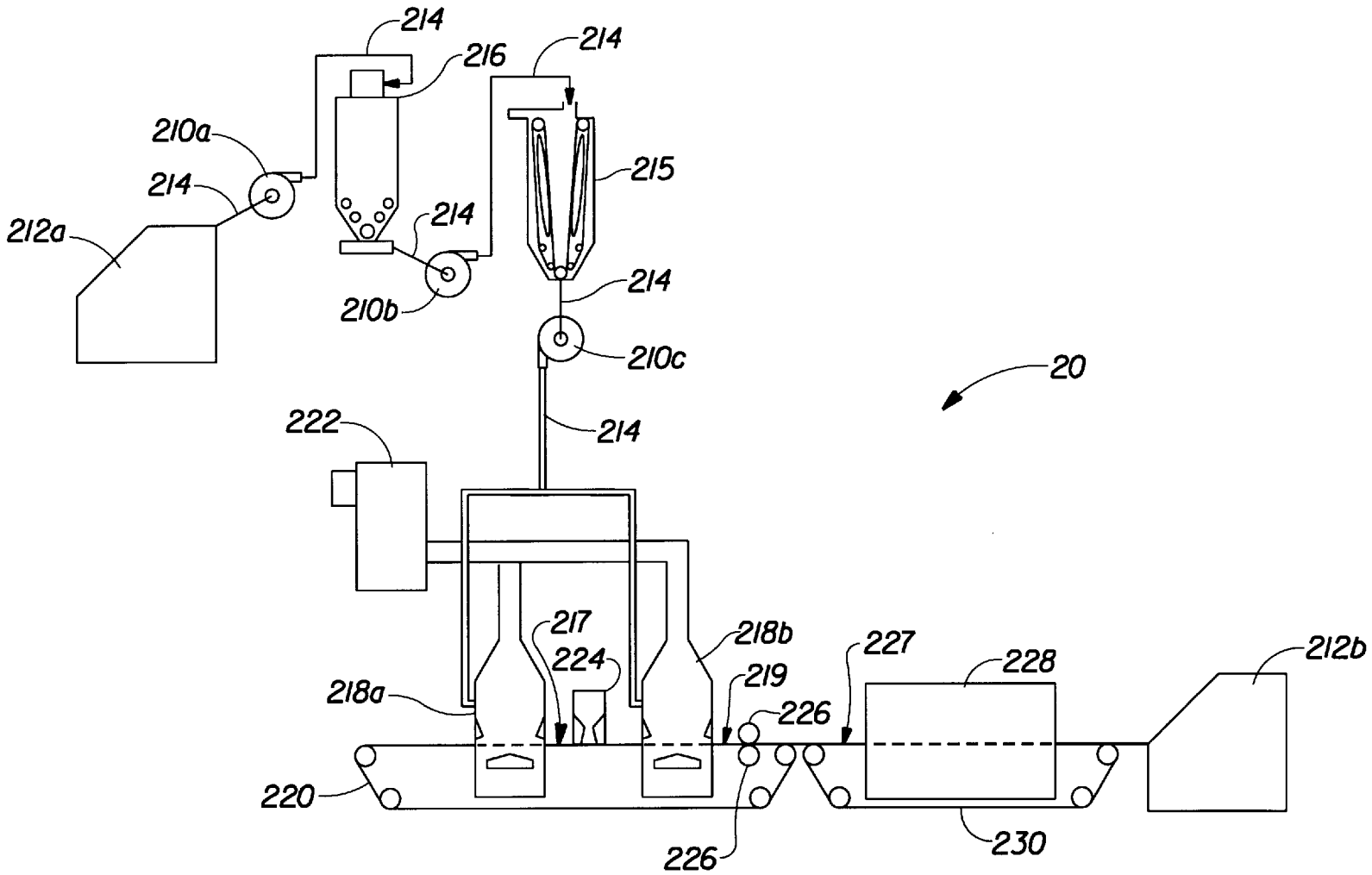
FIG. 2 is an apparatus suitable for use in forming the absorbent composites of the present invention.

An economically preferred apparatus 20 for forming the composites of the present invention is shown in FIG. 2. In general, FIG. 2 shows a system for individualizing chemically stiffened, cellulosic fibers, treating the fibers with a bonding agent, physically associating AGM particles and the treated fibers, adhering the fibers to the AGM, and defibrating the resultant mass to form the composites of the present invention.

As shown in FIG. 2, chemically stiffened, cellulosic fibers are taken from a bale, sheet, or other source of the stiffened fibers and optionally other fibers (not shown) using a fiber opener 212, e.g., a picker type fiber opener such as available from the LaRoche Company of Cours La Ville, France. The fiber opener 212 removes fibers from the bale in substantially individual form. As will be understood by one skilled in the art, some fiber nits or bundles may be present after passing through the fiber opener 212.

The fibers in substantially individual form are transported, e.g., by a first material handling fan 210*a* through a system of fiber transport ducts multiply designated 214 in FIG. 2, to a refiberizing apparatus 216. The material handling fan 210*a*, like the other material handling fans in the apparatus 20, further opens the fibers and transports them to the next stage of the apparatus. A suitable material handling fan is available from Northern Blower Inc., Winnipeg, Manitoba, Canada, as Model LS WHL. The fiberizing apparatus 216 further opens the fibers, i.e., it forms a lower density "fluff" of the fibers and tends to individualize the fibers in any fiber nits or bundles that may be present. A suitable refiberizing apparatus 216 for use herein is an Ospray Surge Bin, available from the Ospray Corporation of Atlanta, Ga.

The fibers are then transported, e.g., through fiber transport ducts 214 by a second material handling fan 210*b*, to a fiber compacting apparatus 215. The fiber compacting apparatus 215 functions to provide a substantially uniform density to the fibers in opened form. The desired density will depend on the desired weight of fibers which is desired to be present in the final composite. The fiber compacting apparatus settings and indeed the need for this apparatus can be selected by one having ordinary skill in the art depending on the particular density which is desired. A suitable fiber compacting apparatus 215 is a LaRoche Vertical Mat Former available from the LaRoche Company of Cours La Ville, France.

The fiber opener 212, material handling fans 210*a* and 210*b*, refiberizing apparatus 216, and compacting apparatus 215 serve to provide the fibers in a substantially homogeneous, opened form (i.e., the fibers are provided in a substantially uniform density with a low level of nits or knots). The specific apparatus employed to provide the fibers will depend on the weight and condition of fibers which is desired to be present in the final composite. It will typically be desired to at least partially defibrate the fibers, preferably to substantially individualize the fibers, in order to ensure a low level of knots and nits and to ensure an even distribution of the bonding agent on the fibers. The skilled artisan can select from the various defibrating and compacting devices such as are known or become known in the art to provide the fibers in the desired form.

The individualized, compacted fibers are then transported, e.g., via third material handling fan 210*c* through fiber transport ducts 214, to fiber air-lay down forming apparatii 218*a* and 218*b* such as are known in the art. The fiber air-lay down apparatii 218*a* and 218*b* serve to form a substantially uniform, air-laid web of the fibers. A preferred fiber lay down apparatus 218 for use in the present invention is a Dan Web fiber lay down apparatus, available form Dan Web Air Forming Systems, Dan Web Forming International, Ltd., Risskov, Denmark. The Dan Web fiber lay down apparatus is well known in the art to have a first, perforated roll and a second roll having picks or needles. The rolls rotate toward each other in the manner of conventional combining rolls. As the fibers pass from the fiber transport ducts 214 through the Dan Web apparatus, the fibers are further opened, i.e., the density of the "fluff" is further decreased. The web of fibers can alternatively be prepared by other methods such as are known or become known in the art, for example, wet-laying.

A bonding agent is applied to the fibers while in the air-laydown forming apparatii 218*a* and 218*b*. The bonding agent is provided by the bonding application station 222, which can be any apparatus suitable for conveying the bonding agent to the air-laydown forming apparatus, for example, humidification chambers or spray chambers such as are known in the art. The air-laydown forming apparatus 218 serves to ensure even distribution of the bonding agent on the chemically stiffened, cellulosic fibers.

The fibers having bonding agent applied thereon are laid down by the first fiber lay down apparatii 218*a* onto conveyor 220 to form a web 217 of the fibers on the conveyor 220. The conveyor 220 can be any as are known in the art of web formation, for example a vacuum conveyor or an electrostatic conveyor.

As shown in FIG. 2, an AGM disperser 224 is situated intermediate the air laydown forming apparatii 218*a* and 218*b*. The AGM disperser 224 deposits particles of AGM onto the fiber web 217 formed by the first air-laydown forming apparatus 218*a*. The AGM disperser 224 dispenses the AGM particles in substantially individual form onto the web 217. The AGM disperser 224 can be any of the apparatus as are known in the art of particle deposition. For example, a Norson AGM Disperser, available from the Nordson Corporation of Duluth, Ga., is suitable for use herein.

The fiber web 217 having AGM particles deposited thereon then passes by the second air-laydown forming apparatus 218*b* where a second layer of chemically stiffened, cellulosic fibers having bonding agent distributed thereon is deposited adjacent the layer of AGM particles, to thereby form a trilayer web 219 of the two fiber webs having bonding agent distributed thereon and AGM particles deposited therebetween.

Means for agitating the trilayer web during its formation (not shown) may be employed to assist in keeping the fibers relatively open. For example, beater bars such as are known in the art may be positioned along the conveyor 220, which beater bars vibrate the web components.

The trilayer web 219 then moves through a set of calendar rolls 226. The calendar rolls 226 combine and compact the fiber webs, thereby ensuring intimate contact between the fibers, bonding agent, and AGM particles, and wrapping of the fibers around the AGM particles.

As shown in FIG. 2, the resultant compacted web 227 is then transported through a drying station 228 by a drying conveyor 230. In the drying station 228, the web 227 is subjected to conditions, typically elevated temperatures and/or vacuum, sufficient to dry or cure the bonding agent. The drying station 228 can be any apparatus which is capable of performing this function, for example any oven such as are known in the art. A preferred type of drying station is a through-air drying oven, for example, as is available from ASEA Brown Boveri of Knoxville, Tenn.

From the drying station 228, the web 227 is transported to another fiber opener 212. The fiber opener can be any type suitable for opening the fibers, e.g., a fan type (impaction) or picker type. Preferably, the fiber opener 212 is a picker type The fiber opener 212 opens the web, substantially separating the fibers which have the AGM particles adhered thereto, to form the absorbent composites of the present invention (it is to be understood that any means that is suitable for separating the fibers after the drying station, to thereby form the absorbent composites herein, may be employed). Thus, substantially individual units comprised of substantially individual AGM particles wrapped by chemically stiffened, cellulosic fibers are formed. (By "substantially individual units," it is meant that the fibers wrapping one AGM particle are substantially separated from other fibers wrapping other AGM particles as previously described, so as to form relatively discrete units of AGM wrapped by fibers. It should be understood that some fiber bonding may occur between fibers wrapped around different AGM particles.) The material is preferably then transported, for example, through another material handling fan (not shown), which further separates the fibers having the AGM particles adhered thereto. From the material handing fan, the composites may be collected, for example, into a bale or container (not shown).

Alternatively, the web 227 can be wound into a roll. The web 227 can be unwound and passed through a fiber opener and preferably a material handling fan, as described above, at a later time to form the composites of the present invention. In either case, the absorbent composites may be used directly in an in-line process, or collected for later use.

In an alternative embodiment, preparation of the absorbent composite involves the formation of a web of the chemically stiffened, cellulosic fibers, for example by air-laying or other suitable method, followed by application of the bonding agent to the web, followed by deposition of the AGM particles on the web and compaction of the web and particles to cause fiber wrapping of the particles. The composite according to this embodiment can be formed using an apparatus substantially as shown in FIG. 2, but wherein only one bonding application station is needed and is positioned between the first air-laydown forming apparatus and the AGM disperser such that the fiber web is formed prior to application of the bonding agent, followed deposition of the AGM particles onto the web. The fiber web having bonding agent and AGM particles deposited thereon then moves through the calendar rolls, which cause fiber wrapping of the particles, a drying station, and a fiber opener as previously described in relation to FIG. 2 to form the absorbent composites of the present invention. The composites are preferably passed through a material handling fan as previously described in relation to FIG. 2.

In yet another embodiment, two or more webs of fibers are formed, followed by the application of bonding agent to the webs and deposition of AGM particles thereon, followed by the combination of the webs, for example, by using combining rolls such as are well known in the art. The combined webs are compacted together prior to the drying station to cause fiber wrapping of the particles, using, for example, a set of calendar rolls. The compacted webs then move through the drying station and fiber opener as previously described in relation to FIG. 2 to form the absorbent composites of the present invention. The composites are preferably passed through a material handling fan as previously described in relation to FIG. 2.

It will be understood by the skilled artisan that any number of fiber webs and AGM layers can be combined in the foregoing manner, and consistent with the teachings herein, to form the absorbent composites of the present invention. The composites of the present invention can also be formed by several alternative methods. Suitable alternative methods are disclosed in the above-referenced U.S. Pat. Nos.3,901,235; 5,002,814; and 5,230,959.

In one alternative method of the present invention, the composite is formed by mixing the AGM particles with the fibers which have been treated with the bonding agent. Mixing can be caused, for example, by the use of any stirring equipment such as known in the art, or by air entrainment. Suitable mixing procedures are described, for example, in the above-referenced U.S. Pat. Nos. 3,901,236; 5,002,814; and 5,230,959. Mixing causes the fibers to wrap around the AGM particles. Bonding is then caused as described herein, for example, by drying the mixture and/or allowing or causing the bonding agent to react with the fibers and particles. The composite is preferably dried, either while or after bonding occurs. Drying may be achieved by any suitable method, for example, by applying heat or by subjecting the composite to infra-red radiation.

The resultant composite contains chemically stiffened fibers wrapped around and adhered to the AGM particles. An absorbent composite 10 of the present invention, made by a process described in the above-referenced U.S. Pat. No. 5,002,814, is shown in FIG. 1, which is a Scanning Electron Micrograph of the absorbent composite taken at a magnification of 85×. As shown and previously described, the composites are substantially individual units comprised of substantially individual AGM particles ("cores") wrapped by chemically stiffened, cellulosic fibers.

Due to the relatively large diameter or cross-section of the AGM particles relative to the fibers, the fibers are in effect adhered to the AGM particles in the resultant composite. The individual fibers are substantially unbonded except to the AGM particles. Similarly, the individual AGM particles are substantially unbonded except to the fibers.

At least a portion of substantially all, preferably all, of the chemically stiffened, cellulosic fibers are disposed on or near at least a portion of the surface of the individual particles of absorbent gelling material. The fibers are disposed such that at least one fiber end, preferably both fiber ends, protrudes from the surface of the particles. Without intending to be bound by theory, it is believed that protrusion of the fiber assists in minimizing migration of the composite in absorbent articles incorporating the composite. The fibers wrapped around a given AGM particle are substantially separated from the fibers wrapped around other AGM particles, as previously described.

The absorbent composites of the present invention are particularly useful in absorbent members for disposable absorbent articles. It should be understood, however, that the composites and absorbent members containing the same can be used for many purposes in many other fields of use. For example, the absorbent composites of the present invention can be used for packing containers, drug delivery devices, wound cleaning devices, burn treatment devices, ion exchange column materials, construction materials, agricultural or horticultural materials such as seed sheets or water-retentive materials, and industrial uses such as sludge or oil dewatering agents, materials for the prevention of dew formation, desiccants, and humidity control materials.

As used herein, the term "absorbent article" refers to devices which absorb and contain body exudates, and more specifically, refers to devices which are placed against the skin of a wearer to absorb and contain the various exudates discharged from the body. The term"disposable" is used herein to describe absorbent articles which are not intended to be laundered or otherwise restored or reused as an absorbent article after a single use. Examples of disposable absorbent articles include feminine hygiene garments such as sanitary napkins and panti-liners, diapers, incontinence briefs, diaper holders, training pants, and the like.

Disposable absorbent articles typically comprise a liquid pervious topsheet, a liquid impervious backsheet joined to the topsheet and an absorbent core positioned between the topsheet and the backsheet. Disposable absorbent articles and components thereof, including the topsheet, backsheet, absorbent core, and any individual layers of these components, have a body surface and a garment surface. As used herein, "body surface" means that surface of the article or component which is intended to be worn toward or adjacent to the body of the wearer, while the "garment surface" is on the opposite side and is intended to be worn toward or placed adjacent to the wearer's body or undergarments when the disposable absorbent article is worn.

The composites of the present invention are particularly useful for use in the absorbent core of disposable absorbent articles. In general, the composites may be used in the same manner for which conventional absorbent gelling materials have been used, for example, in laminates, in relatively high density cores (i.e., compacted, calendared, densified, etc. cores), or in relatively low density cores (i.e., not compacted, for example, air-laid cores). However, the absorbent composite provides certain advantages over conventional particulate absorbent materials. In particular, the absorbent composite has a reduced tendency to migrate within and/or out of the absorbent article, and a reduced tendency to cause pinholing. With conventional particulate absorbent materials, heavy calendaring is typically required in order to minimize migration of the particles. As a result, the potential absorption capacity and absorption rate of the absorbent core, based on the theoretical absorption capacities and rates of the components of the absorbent core, is not realized. In addition, the calendared absorbent core tends to be stiff or "boardy," and pinholing is more likely to occur. Moreover, the particulate material may still migrate within and/or out of the absorbent article. Therefore, a secondary topsheet is often included to minimize the potential for gel on skin and/or to increase the wearer's comfort. In contrast, the absorbent composites of the present invention have a lesser tendency to migrate within and out of the absorbent core. Therefore, absorbent cores containing the absorbent composites of the present invention may not require heavy calendaring to minimize migration of the particles of absorbent gelling material. The uncalendared absorbent core tends to have a uniform, relatively low fiber density, i.e., the core has a relatively open structure. Thus, the uncalendared core tends to have better fluid acquisition properties (e.g., rate and quantity of fluid absorbed in a given time period) than a calendared core. Such cores also tend to be more conformable than calendared cores containing conventional AGM. The need for a secondary topsheet is minimized since migration is minimized and since the particles of AGM are cushioned by the fibers. In addition, the problem of pinholing associated with calendaring may be avoided.

The following description generally discusses the absorbent core, topsheet, and backsheet materials that are useful in disposable absorbent articles. It is to be understood that this general description applies to these components of the specific absorbent articles shown in FIGS. 3–5 and further described below, in addition to those of other disposable absorbent articles which are generally described herein.

The absorbent core comprises the absorbent composite of the present invention. The absorbent core contains at least one absorbent member that includes the composite. As used herein, "absorbent member" means an absorbent structure that is capable of transporting liquids between its structural elements. The term "structural elements" as used herein refers to the individual absorbent composites of the present invention and other materials which may comprise the absorbent structure, for example, fibers, yarns, strands, loose particles, and the like. As used herein, the term "structure" includes the term "structures" and the terms "layer", "layers", and "layered". An absorbent member is not necessarily limited to a web or the like in the form of a single layer or sheet of material. The absorbent member may actually comprise laminates, webs, or combinations of several sheets or webs of the types of the absorbent materials herein described.

The absorbent member can consist essentially of the absorbent composite of the present invention, for example, a web of the composite. Alternatively, the absorbent members of the present invention may contain other materials, for example, absorbent materials that are commonly used in disposable absorbent articles such as the materials described below. In a preferred embodiment, the absorbent member contains the absorbent composite and a carrier mans for the composite. The carrier means is a structure or matrix that the absorbent composite may be located or dispersed in, or on. The carrier means preferably contains an absorbent material, more preferably hydrophilic fibers, such as those described herein. The absorbent composite may be substantially homogeneously (uniformly) dispersed throughout the carrier means or a portion of the carrier means. Alternatively, the absorbent composite may be dispersed in various weight ratios throughout different regions and throughout the thickness of the carrier means. In yet another alternative embodiment, the absorbent composite may be distributed in regions or zones which have higher concentrations of the absorbent composite than do other regions or zones of the carrier means.

The absorbent members of the present invention can be formed by any process or technique that provides an integral absorbent structure. For example, the absorbent members can be formed by a process or technique that provides a web of the absorbent composite or a web comprising a combination of the absorbent composite and fiber material (in the case of a fibrous carrier means). Suitable processes include particle deposition processes, wet-laying and air-laying. The absorbent members are preferably formed by air-laying the absorbent composite, the fiber materials, or a mixture thereof so as to form a structure consisting essentially of the absorbent composite, or a structure having the absorbent composite located or dispersed in, or on the fibers. A procedure for air-laying a mixture of fibers and superabsorbent hydrogel-forming material particles which can be readily adapted by the skilled artisan for use herein is described more fully in U.S. Pat. No. 4,610,678, entitled "High-Density Absorbent Structures" issued to Weisman et al. on Sep. 9, 1986, incorporated herein by reference. Several layers of the absorbent composite and a suitable carrier means may be formed.

As will be understood by the skilled artisan, the degree of fiber bonding between the fibers wrapping a given AGM particle and fibers wrapping other AGM particles will depend on the degree of calendaring or embossing of the absorbent member, and the presence of components other than the absorbent composite in the member. For example, where an absorbent member consists essentially of a web of the absorbent composite and is calendared or embossed, there may be a substantial amount of fiber bonding between fibers wrapping different AGM particles in the embossed or calendared area. Where the absorbent composite is substantially homogeneously dispersed throughout a web containing hydrophilic fibers, the fibers wrapping a given AGM particle tend to remain substantially separated from fibers wrapping other particles. The amount of fiber bonding tends to increase as the amount of absorbent composite in the web increases, or where the web is calendared or embossed.

In general, the absorbent core is capable of absorbing or retaining liquids (e.g., menses, urine, and/or body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, asymmetric, etc.). In addition to the absorbent composites of the present invention, the absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones and/or have a profile so as to be thicker in the center, hydrophilic gradients; gradients of the absorbent composite of the present invention, superabsorbent gradients; or lower average density and lower average basis weight zones, e.g., acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, incontinence pads, pantiliners, regular sanitary napkins, and overnight sanitary napkins, and to accommodate wearers ranging from infants to adults.

The absorbent core comprises at least one absorbent member comprising the absorbent composite of the present invention. Thus, the absorbent core may consist essentially of the absorbent composite of the present invention. In a preferred embodiment, the absorbent core has at least one absorbent member which comprises the absorbent composite and a carrier means for the composite, such as previously described. The carrier means preferably comprises a fibrous web or batt that contains entangled masses of hydrophilic fibers. The absorbent composite is preferably substantially homogeneously (uniformly) dispersed throughout the carrier means or a portion of the carrier means. The absorbent properties of such absorbent members may thus be generally uniform throughout the member. Alternatively, the absorbent composite and hydrophilic fibers can be dispersed so as to form gradients or zones of differential absorption capacity and/or rate in the absorbent member. The absorbent member may be calendared or embossed.

As used herein, the term "hydrophilic" describes fibers or the surfaces of fibers which are wetted by the liquids deposited onto the fibers. As discussed in detail in The American Chemical Society publication entitled *Contact Angle, Wetability, and Adhesion* edited by Robert F. Gould and copyrighted in 1964, a fiber or surface of a fiber is said to be wetted by a liquid either when the contact angle between the liquid and the fiber or surface is less than 90° or when the liquid will tend to spread spontaneously across the surface of the fiber, both conditions normally coexisting.

Any type of hydrophilic fibrous material which is suitable for use in conventional absorbent products are suitable for use in the absorbent core herein. Specific examples of such hydrophilic fibrous materials include cellulose fibers, modified cellulose fibers, chemically stiffened cellulose fibers such as those described herein for forming the absorbent composite of the present invention, rayon, polyester fibers such as polyethylene terephthalate (DACRON), hydrophilic nylon (HYDROFIL), polymeric bicomponent fibers, and the like. Other examples of suitable hydrophilic fibrous materials include hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. For reasons of availability and cost, cellulose fibers, in particular comminuted wood pulp (i.e., airfelt), are preferred for use in the absorbent core, particularly the storage layer described herein.

The amount of composite included in the absorbent core is generally selected based on the amount of absorbent gelling material that is desired in the article, which is itself generally selected based on the absorptive capacity and absorptive rate that is desired in the article. The relative amount of absorbent gelling material and hydrophilic fibers used in absorbent members can be most conveniently expressed in terms of a weight percentage of the absorbent member. Typically, absorbent gelling materials are used with hydrophilic fibers in an amount ranging from about 2% to about 90%, preferably about 30% to about 85%, more preferably about 30% to about 70%, most preferably from about 40% to about 70, AGM and correspondingly, about 10% to about 98%, preferably from about 70% to about 15%, more preferably from about 70% to about 30%, most preferably from about 60% to about 30%, hydrophilic fibers. The relative amounts of the absorbent composite and any hydrophilic fibers (including those making up the composite) can be selected to achieve these ranges. In order to minimize the thickness of the absorbent article, it may be desired to maximize the concentration of AGM in certain absorbent members, particularly an absorbent member to be used for fluid storage.

The absorbent core can include other absorbent components that are often used in absorbent articles, for example, a dusting layer, a wicking or acquisition layer, or a secondary topsheet for increasing the wearer's comfort.

The topsheet is preferably compliant, soft feeling, and non-irritating to the wearer's skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. A suitable backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Film Products of Terre Haute, Ind., under the designation XP-39385. The backsheet is preferably embossed and/or matte finished to provide a more clothlike appearance. Further, the backsheet may permit vapors to escape from the absorbent core (i.e., the backsheet is breathable) while still preventing exudates from passing through the backsheet. The size of the backsheet is dictated by the size of the absorbent core and the exact absorbent article design selected.

The backsheet and the topsheet are positioned adjacent the garment surface and the body surface, respectively, of the absorbent core. The absorbent core is preferably joined with the topsheet, the backsheet, or both in any manner as is known by attachment means (not shown in FIGS. 3–5) such as those well known in the art. However, embodiments of the present invention are envisioned wherein portions of the entire absorbent core is unattached to either the topsheet, the backsheet, or both.

For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258or H-2031. The attachment means will preferably comprise an open pattern network of filaments of adhesive as is disclosed in U.S. Pat. No. 4,573,986, issued to Minetola, et al. Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. 3,911,173 issued to Sprague, Jr. on Oct. 7, 1975; U.S. Pat. No. 4,785,996 issued to Zwieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

Figure 3:
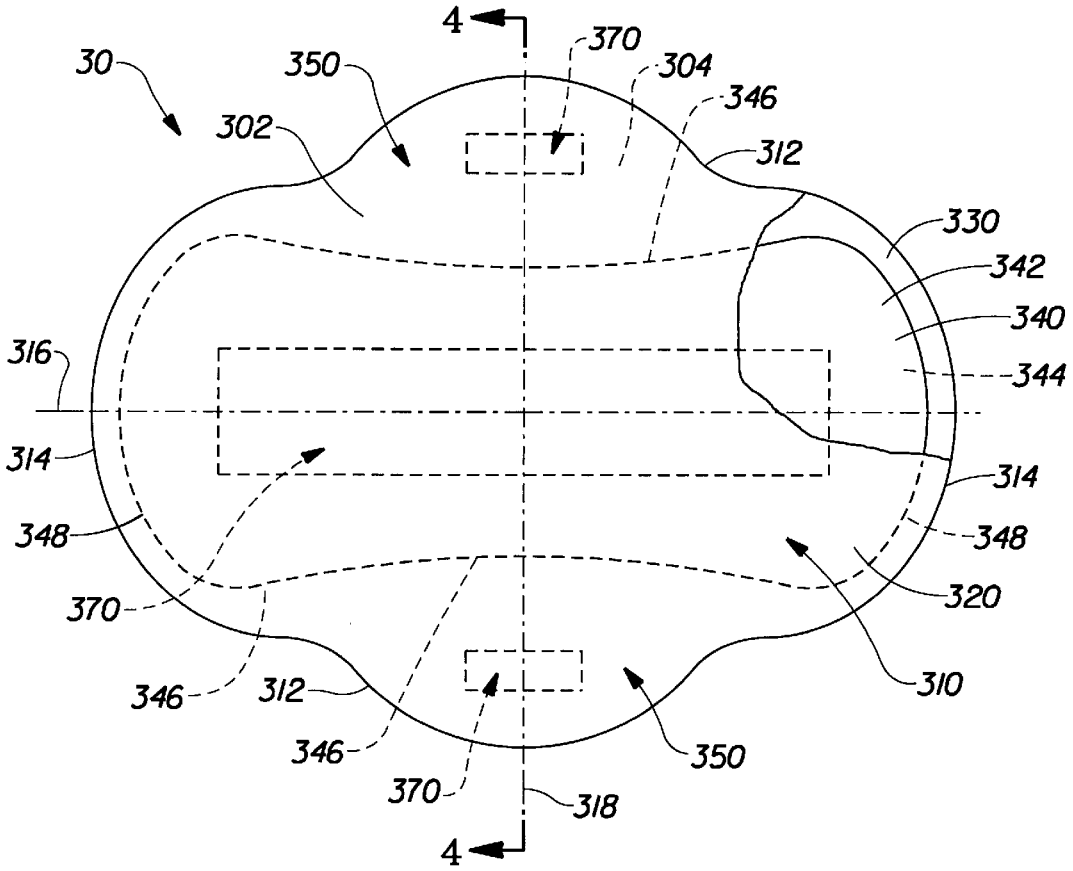
FIG. 3 is an absorbent article in the form of a sanitary napkin according to the present invention.

A preferred embodiment of a unitary disposable absorbent article of the present invention is the catamenial pad, sanitary napkin 30, shown in FIG. 3. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads including diapers, and the like.

FIG. 3 is a plan view of the sanitary napkin 30 of the present invention in its flat-out state with portions of the structure being cut-away to more clearly show the construction of the sanitary napkin 30 and with the portion of the sanitary napkin 30 which faces or contacts the wearer, oriented towards the viewer. The sanitary napkin 30 has two surfaces, a body-contacting surface 302 or "body surface" and a garment surface 304. The sanitary napkin 30 is shown in FIG. 3 as viewed from its body surface. The body surface is intended to be worn adjacent to the body of the wearer while the garment surface is on the opposite side and is intended to be placed adjacent to the wearer's undergarments when the sanitary napkin 30 is worn. As shown in FIG. 3, the sanitary napkin 30 preferably comprises a central absorbent body 310 and an undergarment protection system 350.

The central absorbent body 310 comprises a liquid pervious topsheet 320, a liquid impervious backsheet 330 joined with the topsheet 320, and an absorbent core 340 positioned between the topsheet 320 and the backsheet 330. FIG. 3 also shows that the central absorbent body 310 has a periphery which is defined by the outer edges of the central absorbent body 310 in which the longitudinal edges are designated 312 and the end edges are designated 314. The central absorbent body 310 further has a longitudinal centerline 316 and a transverse centerline 318. The term "longitudinal", as used herein, refers to a line, axis or direction in the plane of the absorbent article that is generally aligned with (e.g., approximately parallel to) a vertical plane which bisects a standing or upright wearer into left and right body halves when the absorbent article is worn. The terms "transverse" or "lateral" as used herein, are interchangeable, and refer to a line, axis or direction which lies within the plane of the absorbent article that is generally perpendicular to the longitudinal direction. As shown in FIG. 3, the absorbent core 340 has a body surface 342, a garment surface 344, side edges 346, and end edges 348.

In general, the construction of the topsheet 320, backsheet 330, and absorbent core 340 is as described herein above. The topsheet, the backsheet, and the absorbent core may be assembled in a variety of well known configurations (including so called "tube" products), with the absorbent core being adapted to include the absorbent composites of the present invention. Preferred sanitary napkin configurations are described generally in U.S. Pat. No. 4,950,264, "Thin, Flexible Sanitary Napkin" issued to Osborn on Aug. 21, 1990; U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987, U.S. Pat. No. 5,009,653 "Thin, Flexible Sanitary Napkin" issued to Osborn on Apr. 23, 1991, and U.S. Pat. No. 5,308,346 "Elasticized Sanitary Napkin" issued to Sneller, at al. on May 3, 1994. Each of these patents are hereby incorporated herein by reference. FIG. 3 shows a preferred embodiment of the sanitary napkin 30 in which the topsheet 320 and the backsheet 330 have length and width dimensions generally larger than those of the absorbent core 340. The topsheet 320 and the backsheet 330 extend beyond the edges of the absorbent core 340 to thereby form portions of the periphery.

Exemplary absorbent structures for use as the absorbent core in sanitary napkins and which can be adapted to the present invention are described in the above referenced and incorporated U.S. Pat. No. 4,610,678, and in U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Proctor & Gamble Company, published Oct. 22, 1986 in the name of Duenk, et al. The absorbent cores described in these patents can be readily adapted to include the absorbent composites as an absorbent gelling material therein described. A preferred embodiment of the absorbent core of the present invention comprises a layer of superabsorbent material disposed between two air laid tissues as described in the above referenced and incorporated U.S. Pat. No. 4,950,264 and U.S. Pat. No. 5,009,653, wherein the superabsorbent material includes the absorbent composites of the present invention. Each of these patents are incorporated herein by reference. The absorbent core may alternatively comprise a web comprising hydrophilic fibers and the absorbent composite, as described above in general reference to absorbent articles.

A preferred topsheet 320 for the sanitary napkin 30 comprises an apertured formed film. Apertured formed films are preferred for the topsheet because they are pervious to body exudates and yet are nonabsorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structure Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred topsheet for the present invention is the formed film described in one or more of the above patents and marketed on sanitary napkins by The Proctor & Gamble Company of Cincinnati, Ohio as "DRI-WEAVE".

In a preferred embodiment of the sanitary napkins 30 of present invention, the body surface of the formed film topsheet 320 is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, the topsheet can be made hydrophilic by treating it with a surfactant such as is described in the above referenced and incorporated U.S. Pat. Nos. 4,950,254 and 5,009,653.

Figure 4:
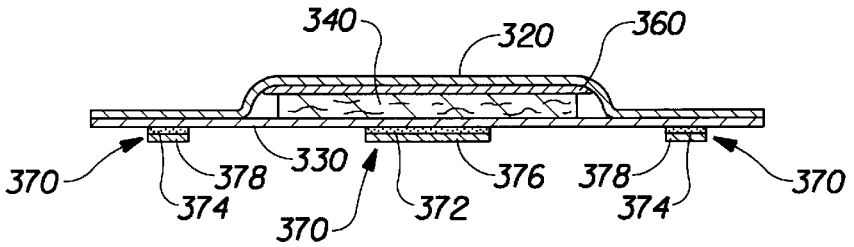
FIG. 4 is a cross-sectional view along the line 4—4 of FIG. 3.

In the preferred embodiment of the present invention shown in FIG. 4, an acquisition component 360 (or components) may either be positioned between the topsheet 320 and the absorbent core 340, or comprise the bottom surface of a composite topsheet. The acquisition component may serve several functions. These functions include improving wicking of exudates over and into the absorbent core. The improved wicking of exudates is important because it provides a more even distribution of the exudates throughout the absorbent core and allows the sanitary napkin 30 to be made relatively thin. (The wicking referred to herein may encompass the transportation of liquids in one, two, or all directions (i.e., in the x-y plane and/or in the z-direction). The acquisition component 360 may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition component are more fully described in the above referenced and incorporated U.S. Pat. Nos. 4,950,264 and 5,009,653; and in PCT patent publication WO 93/11725 "Absorbent Article Having Fused Layers", published in the name of Cree, et al. on Jun. 24, 1993; and copending U.S. patent application Ser. No. 08/289,084, filed May 6, 1994 in the name of Cree et al. Each of these references is incorporated herein by reference. In a preferred embodiment, the acquisition component 360 may be joined with the topsheet 320 by any of the conventional means for joining webs together, most preferably by fusion bonds as is more fully described in the above-referenced Cree et al. patent application and PCT publication.

In use, the sanitary napkin 30 can be held in place by any attachment means 370 well-known for such purposes. Preferably, the sanitary napkin is placed in the user's undergarment or panty and secured thereto by a fastener such as an adhesive. The adhesive provides a means for securing the sanitary napkin in the crotch portion of the undergarment Thus, a portion or all of the garment surface 304 of the sanitary napkin 30 may be coated with adhesive. For the preferred embodiment of the present invention shown in FIG. 3, a portion is disposed on both the central absorbent body 310 and the undergarment protection system 350 of the sanitary napkin 30. That portion of the adhesive disposed on the central absorbent body is identified as the pad adhesive 372 and that portion disposed on the undergarment protection system is identified flap adhesive 374 depending on which element of the undergarment protection system whereon the adhesive is disposed. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697 issued to Osborn et al. on Apr. 17, 1990. The pressure-sensitive adhesive is typically covered with a removable release liner in order to keep the adhesive from adhering to a surface other than the crotch portion of the undergarment prior to use. These are identified as the pad release liner 376 and the flap release liner 378 in FIG. 4. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. Suitable release liners are also described in the above-referenced U.S. Pat. No. 4,917,697. The sanitary napkin 30 of the present invention is used by removing the release liner and thereafter placing the sanitary napkin in an undergarment so that the adhesive contacts the undergarment. The adhesive maintains the sanitary napkin in its position within the undergarment during use.

The sanitary napkin of the present invention may further comprise an undergarment protection system 350, for example, side flaps. The flaps serve at least two purposes. First, the flaps help serve to prevent soiling of the wearer's body and underwear by menstrual fluid, preferably by forming a double wall barrier along the edges of the undergarment. Second, the flaps are preferably provided with a portion of the attachment means 370 the flap adhesive 374, on their garment surface so that the flaps can be folded back under the undergarment and attached to the garment facing side of the undergarment or to each other. In this way, the flaps serve to keep the sanitary napkin property positioned in the undergarment. The flaps can be constructed of various materials including materials similar to the topsheet, backsheet, tissue, or combination of these materials. A number of sanitary napkins having flaps suitable or adaptable for use with the sanitary napkins of the present invention are disclosed in the above referenced and incorporated U.S. Pat. No. 4,589,876; and in U.S. Pat. No. 4,687,478 entitled "Shaped Sanitary Napkin With Flaps", which issued to Van Tilburg on Aug. 18, 1987 and U.S. Pat. No. 4,608,047, entitled "Sanitary Napkin Attachment Means", which issued to Mattingly on Aug. 26, 1986. Each of these patents are incorporated herein by reference.

Another disposable absorbent article in which the absorbent composites herein may be used are diapers. As used herein, the term "diaper" refers to an absorbent article generally worn by infants and incontinent persons that is worn about the lower torso of the wearer.

Figure 5:
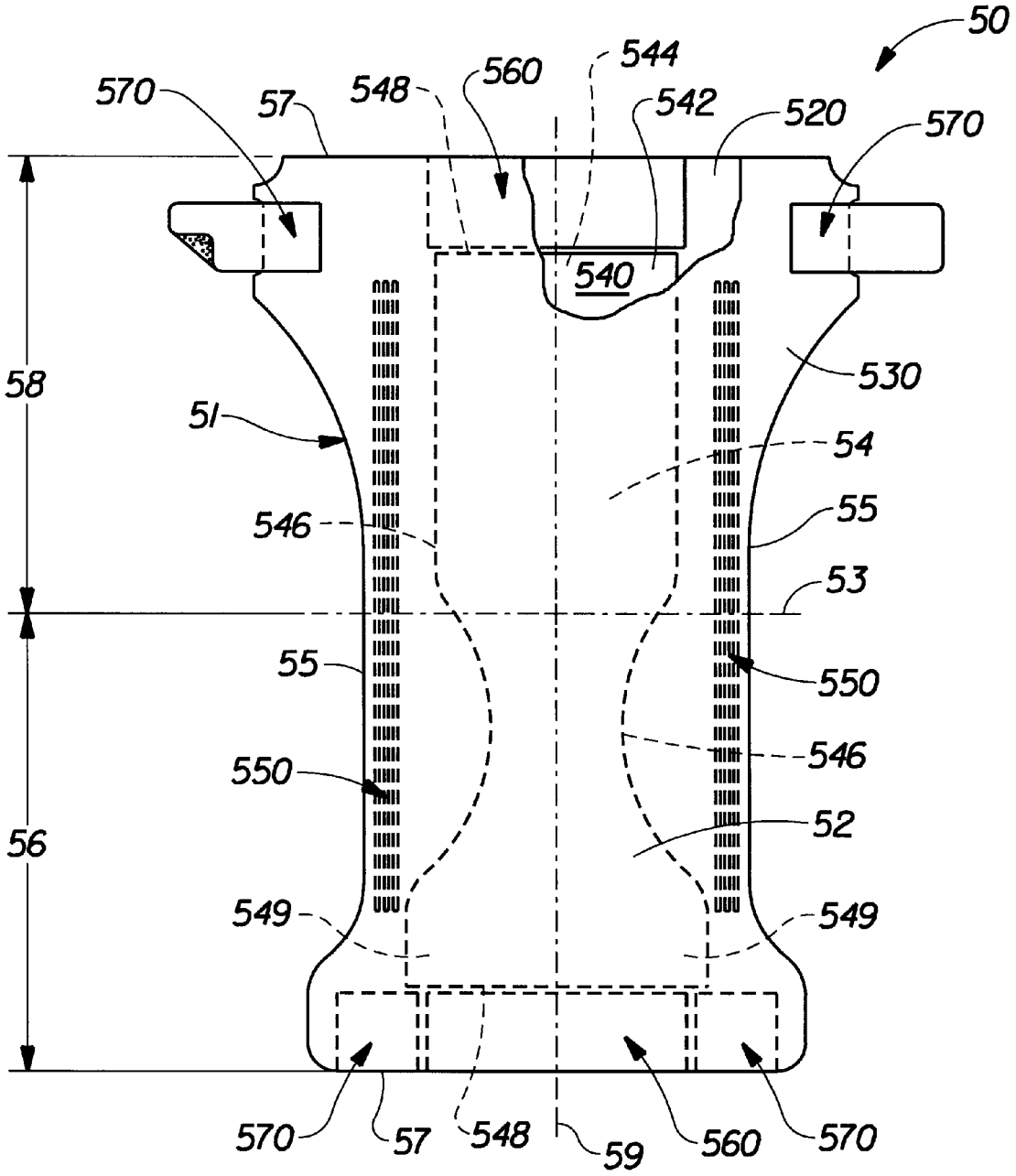
FIG. 5 is an absorbent article in the form of a diaper according to the present invention.

FIG. 5 is a plan view of the diaper 50 of the present invention in its flat-out, uncontracted state (i.e., with elastic induced contraction pulled out) with portions of the structure being cut-away to more clearly show the construction of the diaper 50 and with the portion of the diaper 50 which faces away from the wearer, the outer surface, oriented towards the viewer. As shown in FIG. 5, the diaper 50 preferably comprises a liquid pervious topsheet 520; a liquid impervious backsheet 530 joined with the topsheet 520; an absorbent core 540 positioned between the topsheet 520 and the backsheet 530, the absorbent core 540 having a garment facing surface 542, a body facing surface 544, side edges 546, waist edges 548, and ears 549. The diaper 50 preferably further comprises elasticized leg cuffs 550; an elastic waist feature multiply designated as 560; and a fastening system generally multiply designated as 570.

The diaper 50 is shown in FIG. 5 to have an outer surface 52, an inner surface 54 opposed to the outer surface 52, a first waist region 56, a second waist region 58, and a periphery 51 which is defined by the outer edges of the diaper 50 in which the longitudinal edges are designated 55 and the end edges are designated 57. (While the skilled artisan will recognize that a diaper is usually described in terms of having a pair of waist regions and a crotch region between the waist regions, in this application, for simplicity of terminology, the diaper 50 is described as having only waist regions including a portion of the diaper which would typically be designated as part of the crotch region). The inner surface 54 of the diaper 50 comprises that portion of the diaper 50 which is positioned adjacent to the wearer's body during use (i.e., the inner surface 54 generally is formed by at least a portion of the topsheet 520 and other components that may be joined to the topsheet 520). The outer surface 52 comprises that portion of the diaper 50 which is positioned away from the wearer's body (i.e., the outer surface 52 generally is formed by at least a portion of backsheet 530 and other components that may be joined to the backsheet 530). (As used herein, the portion of the diaper 50 or component thereof which faces the wearer is also referred to as the body facing surface. Similarly, the portion facing away from the wearer is also referred to herein as the garment facing surface.) The first waist region 56 and the second waist region 58 extend, respectively, from the end edges 57 of the periphery 51 to the lateral centerline 53 of the diaper 50. FIG. 5 also shows the longitudinal centerline 59.

FIG. 5 shows a preferred embodiment of the diaper 50 in which the topsheet 520 and the backsheet 530 have length and width dimensions generally larger than those of the absorbent core 540. The elasticized leg cuffs 550 and the backsheet 530 extend beyond the edges of the absorbent core 540 to thereby form the periphery 51 of the diaper 50.

Diapers of the present invention can have a number of well known configurations, with the absorbent cores thereof being adapted to the present invention. Exemplary configurations are described generally in U.S. Pat. No. B1 3,860, 003 issued to Buell on Apr. 18, 1989; U.S. Pat. No. 5,151, 092 issued to Buell et al. on Sep. 29, 1992; and U.S. Pat. No. 5,221,274 issued to Buell et al. on Jun. 22, 1993. Each of these patents is incorporated herein by reference. Another diaper configuration to which the present invention can be readily adapted is described in co-pending U.S. patent application Ser. No. 08/203,456; filed on Feb. 28, 1994 in the name of Roe et al. and incorporated herein by reference. The absorbent cores of diapers described in these patents can be adapted in light of the teachings herein to include the absorbent composite of the present invention as an absorbent gelling material described therein.

A topsheet 520 which is particularly suitable for use in the diaper 50, is carded and thermally bonded by means well known to those skilled in the fabrics art. A satisfactory topsheet for comprises staple length polypropylene fibers having a denier of about 2.2. As used herein, the term "staple length fibers" refers to those fibers having a length of at least about 15.9 mm (0.625 inches). Preferably, the topsheet has a basis weight from about 14 to about 25 grams per square meter. A suitable topsheet is manufactured by Veratec, Inc., a Division of International Paper Company, of Walpole, Mass. under the designation P-8.

The topsheet 520 of diaper 50 is preferably made of a hydrophobic material to isolate the wearer's skin from liquids which have passed through the topsheet and are contained in the absorbent core (i.e. to prevent rewet). If the topsheet is made of a hydrophobic material, at least the upper surface of the topsheet is treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the topsheet material with the surfactant and immersing the material into the surfactant. A more detailed discussion of such a treatment and hydrophilicity is contained in U.S. Pat. Nos. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

In a preferred embodiment of a diaper as described herein, the backsheet 530 has a modified hourglass shape extending beyond the absorbent core a minimum distance of about 1.3 cm to about 6.4 cm (about 0.5 to about 2.5 inch) around the entire diaper periphery.

The absorbent core 540 may take on any size or shape that is compatible with the diaper 50. One preferred embodiment of the diaper 50 has an asymmetric, modified T-shaped absorbent core 540 having ears in the first waist region but a generally rectangular shape in the second waist region. Exemplary absorbent structures for use as the absorbent core of the present invention that have achieved wide acceptance and commercial success are described in the above referenced and incorporated U.S. Pat. No. 4,610,678, and in U.S. Pat. No. 4,673,402 entitled "Absorbent Articles With Dual-Layered Cores" issued to Weisman et al. on June. 16, 1987; U.S. Pat. No. 4,888,231 entitled "Absorbent Core Having A Dusting Layer" issued to Angstadt on Dec. 19, 1989; and the above referenced U.S. Pat. No. 4,834,735. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference. The absorbent cores described in these patents can be adapted to include, as an absorbent gelling material, the absorbent composites of the present invention. Preferably, the absorbent composite will be included in a component of the absorbent core which functions primarily to retain or store fluids, as opposed to acquiring and/or distributing fluids (typically referred to as the storage layer or storage core). More preferably, the absorbent core comprises hydrophilic fibers and the absorbent composite, as described above in general reference to absorbent articles.

In a preferred embodiment, the diaper 50 further comprises elasticized leg cuffs 550 for providing improved containment of liquids and other body exudates; an elastic waist feature 560 that provides improved fit and containment; and a fastening system 570 which forms a side closure which maintains the first waist region 56 and the second waist region 58 in an overlapping configuration such that lateral tensions are maintained around the circumference of the diaper to maintain the diaper on the wearer. The diaper 50 may also comprise elasticized side panels (not shown) in the waist regions 56 and 58 to provide an elastically extensible feature that provides a more comfortable and contouring fit and more effective application of the diaper 50.

The elasticized leg cuffs 550 can be constructed in a number of different configurations, including those described in the above referenced U.S. Pat. No. B1 3,860, 003; U.S. Pat. No. 4,909,803, issued to Aziz et al. on Mar. 20, 1990; U.S. Pat. No. 4,695,278, issued to Lawson on Sep. 22, 1987; and U.S. Pat. No. 4,795,454, issued to Dragoo in Jan. 3, 1989, each being incorporated herein by reference.

The elasticized waist feature preferably comprises an elasticized waistband (not shown) that may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, each of these references being incorporated herein by reference.

The elasticized side panels may be constructed in a number of configurations. Examples of diapers with elasticized side panels positioned in the ears (ear flaps) of the diaper are disclosed in U.S. Pat. No. 4,857,067, issued to Wood, et al. on Aug. 15, 1989; U.S. Pat. No. 4,381,781, issued to Sciaraffa, et al. on May 3, 1983; U.S. Pat. No. 4,938,753, issued to Van Gompel, et al. on Jul. 3, 1990; and U.S. Pat. No. 5,151,092, issued to Buell et al. on Sep. 29, 1992; each of which are incorporated herein by reference.

Exemplary fastening systems 570 are disclosed in U.S. Pat. No. 4,846,815, issued to Scripps on Jul. 11, 1989; U.S. Pat. No. 4,894,060, issued to Nestegard on Jan. 16, 1990; U.S. Pat. No. 4,946,527, issued to Battrell on Aug. 7, 1990; U.S. Pat. No. 3,848,594, issued to Buell on Nov. 19, 1974; U.S. Pat. No. 4,662,875, issued to Hirotsu et al. on May 5, 1987; and U.S. Pat. No. 5,151,092, issued to Buell et al. on Sep. 29, 1992; each of which is incorporated herein by reference.

The diaper 50 is preferably applied to a wearer by positioning one of the waist regions of the diaper, preferably the second waist region 58, under the wearer's back and drawing the remainder of the diaper between the wearer's legs so that the other waist region, preferably the first waist region 56, is positioned across the front of the wearer. The fastening system is then applied to effect a side closure.

The composites of the present invention are useful in the absorbent cores of pantiliners. Exemplary pantiliners for which the present invention may be adapted are disclosed in U.S. Pat. No. 4,738,676 entitled "Pantiliner" issued to Osborn on Apr. 19, 1988, which patent is incorporated herein by reference.

The composites of the present invention are also useful in the absorbent core of training pants. The term "trainingpant", as used herein, refers to disposable garments having fixed sides and leg openings. Training pants are placed in position on the wearer by inserting the wearer's legs into the leg openings and sliding the training pant into position about the wearer's lower torso. Training pants to which the present invention are readily adapted are disclosed in U.S. Pat. No. 5,246,433, issued to Hasse, et al. on Sep. 21, 1993.

Another disposable absorbent article for which the composites of the present invention are useful are incontinence articles. The term "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons. Incontinence articles to which the present invention can be readily adapted are disclosed in U.S. Pat. No. 4,253,461 issued to Strickland, et al. on Mar. 3, 1981; U.S. Pat. Nos. 4,597,760 and 4,597,761 both issued to Buell on Jul. 1, 1986; U.S. Pat. No. 4,704,115 issued to Buell on Nov. 3, 1987; U.S. Pat. No. 4,909,802 issued to Ahr, et al. on Mar. 20, 1990; U.S. Pat. No. 4,964,860 issued to Gipson, et al. on Oct. 23, 1990; and in U.S. Pat. No. 5,304,161, "Absorbent Article Having Rapid Acquiring Multiple Layer Absorbent Core," issued to Ahr on Apr. 19, 1994. The absorbent cores described in these patents can be adapted to include, as an absorbent gelling material, the absorbent composites of the present invention.

EXAMPLES

Absorbent composites are prepared from Nalco 1180 (particles of absorbent gelling material available from Stockhausen GmbH of Krefeld, Germany (hereinafter referred to in the examples as AGM), several fiber materials, and a 10% aqueous solution of Keymene® 557 as bonding agent to bond the AGM and fibers. The fibers are abbreviated as follows:

CSF chemically stiffened, cellulosic fibers formed from Foley fluff (southern kraft pulp, Buckeye Cellulose Co., Memphis, Tenn., USA) having a moisture content of about 7%, which are crosslinked with citric acid to the extent of about 3.8 mole % citric acid on a dry fiber cellulose anhydroglucose basis according to U.S. Pat. No. 5,137,537.

| | |
|---|---|
| PP | POLYSTEEN polypropylene fibers, available from Steen & Co. GmbH, of Schwarzenbek, Germany, being 2 denier and 6 mm in length |
| PE | POLYSTEEN polyethylene fibers, available from Steen & Co. GmbH, of Schwarzenbek, Germany, being 4 denier and 4.6 mm in length |
| BiCo | POLYSTEEN fibers having a polypropylene core, polyethylene outer layer, available from Steen & Co. GmbH, of Schwarzenbek, Germany, being 2.5 denier and 4.6 mm in length |

The percentage of fibers and AGM particles of the composites is shown in Table I. In Table I, Examples 1–5 represent absorbent composites according to the present invention.

The composites are prepared as follows using equipment as described and configured in reference to FIG. 2. The fibers are taken from a bale of the fibers using a fiber opener available from the LaRoche Company. The opened fibers are further opened by an Ospray Surge Bin and then compacted using a Wright Vertical Mat Former. The fibers at this point are 95%–99% open and have a density of 0.1 g/cm$^3$. The resultant individualized fibers are then transported to two Dan Web fiber lay down apparatii.

The Kymene® solution is applied to the fibers while in the Dan Web apparatii using a conventional humidification chamber. The Kymene® solution is applied in an amount of 10–15 weight %, based on the weight of the fibers. Fibers having the Kymene® solution applied thereon are laid down by the first Dan Web apparatii onto a vacuum conveyor. The Dan Web apparatus lays the fiber/Kymene® solution mixture down at a basis weight of 18 g/m$^2$–25 g/m$^2$.

AGM particles are then deposited onto the first fiber web using a Nordson AGM Disperser. The AGM particles are laid down at a basis weight of 0.054 g/m$^2$–0.070 g/cm$^2$. The fiber web having AGM particles deposited thereon then passes by the second Dan Web apparatus where a layer of fibers having Kymene® solution distributed thereon is deposited adjacent the layer of AGM particles. The fiber/Kymene® solution mixture is laid down at a basis weight of 18 g/m$^2$–25 g/m$^2$.

The fiber webs having Kymene® solution distributed thereon and AGM particles deposited therebetween then move through a set of calendar rolls which combine and compact the fiber webs to ensure intimate contact between the fibers, Kymene® solution, and AGM particles. The resultant compacted web is then transported to a through-air drying oven, available from ASEA Brown Boveri. The web is exposed to a temperature of about 300° F. for a period of 1–2 minutes to dry or cure the Kymene® solution.

The resultant web is transported to another fiber opener (LaRoche) which opens the web and separates the fibers which have the AGM particles adhered thereto. The material is then transported through a material handling fan (Northern Blower Inc., Winnipeg, Manitoba, Canada, Model LS WHL), which further separates the fibers having the AGM particles adhered thereto, to thereby form the absorbent composites.

Absorbent composites according to the present invention are made as described in Examples 1–5, except that 10%, by weight, aqueous solutions of propylene glycol, glycerol, or ACCOSTRENGTH 711 are used as the bonding agent.

TABLE I

| Example No. | wt. % AGM | wt. % CSF | wt. % PP | ratio CSF/PP |
|---|---|---|---|---|
| 1 | 50 | 50 | 0 | 100/0 |
| 2 | 50 | 40 | 10 | 80/20 |
| 3 | 50 | 30 | 20 | 60/40 |
| 4 | 65 | 25 | 10 | 71/29 |
| 5 | 65 | 30 | 5 | 86/14 |
| CE 1 | 65 | 0 | 35 | 0/100 |

The following tests are performed at room temperature, unless otherwise indicated.

Absorption Capacity and Fluid Retention of Composites

The Absorption Capacity and Fluid Retention of the absorbent composites is determined as follows. 0.3 grams of the composite is enclosed in a dry, pre-weighed 6 cm×6 cm tea bag formed of a nonwoven. The tea bag is immersed in an excess of sheep's blood for 10 minutes and then removed and allowed to drain. After a draining time of 10 seconds, the tea bag is weighed and the weight is compared to the initial tea bag weight to determine the weight of fluid absorbed by the composite, the Absorption Capacity. The weight is not adjusted for the amount of fluid absorbed by the tea bag itself. The tea bag is then centrifuged at 1400 rpm for 10 minutes. The tea bag is weighed again and the weight is compared to the initial tea bag weight to determine the amount of fluid that is retained by the composite (Fluid Retention). The Absorption Capacity (AC) and Fluid Retention (FR), in grams sheep's blood/gram composite, are calculated as follows:

AC=(tea bag weight after 10 minutes−empty tea bag weight)+(weight dry composite included in tea bag)

FR=(tea bag weight after centrifugation−empty tea bag weight)+(weight dry composite included in tea bag)

Absorption Capacity Under Pressure of Composites

The Absorption Capacity Under Pressure of the absorbent composites is determined as follows. A pre-weighed sample of the composite (approximately 0.9 grams) is placed in a small container with a sieve at the bottom (weight of the sample is $W_i$). A suitable weight is placed on top of the sample to create a pressure of 0.25 psi on the sample. The container and its contents are weighed and placed on a filter plate in a Petri-dish which is filled with sheep's blood at room temperature (20°–25° C.), such that the sieve comes slightly into contact with the blood. After one hour the sample is removed from the container and re-weighed (weight of the sample after 1 hour is $W_a$). The Absorption Capacity Under Pressure (ACUP), in grams sheep's blood/gram composite, is calculated as follows:

$$ACUP = \frac{W_a - W_i}{W_i}$$

Acquisition Time and Acquisition Rate of Composites

The Acquisition Time (AT) of the composite is determined as follows. 5.00±0.15 ml of sheep's blood is delivered to the composite through a fixed area opening in 3.4 seconds under a 0.25 psi load. The time to acquire the sheep's blood, i.e., the Acquisition Time, is recorded using an electronic strike-through plate and timer. A built-in sensory probe detects the presence of the sheep's blood which triggers the start of the timer. When completely drained, the timer stops. The Acquisition Rate (AR) is calculated as follows:

$$AR = \frac{\text{ml sheep's blood delivered to the composite}}{\text{Acquisition Time}}$$

The Fluid Retention, Absorption Capacity Under Pressure, Acquisition Time, and Acquisition Rate of the composites 1–5 and Comparative Example Composite 1 are shown in Table II. Similar results are obtained where PE or Bico is substituted for PP in the Composites 1–5 or the Comparative Example Composite 1.

TABLE II

| Example No. | Fluid Retention, g/g | Absorption Capacity Under Pressure, g/g | Acquisition Time, seconds | Acquisition Rate, ml/second |
|---|---|---|---|---|
| 1 | 23.3 | 33.2 | 19.0 | 0.26 |
| 2 | 23.1 | 36 | 23.7 | 0.21 |
| 3 | 28.1 | 42.2 | 18.0 | 0.28 |
| 4 | 20.9 | 34.4 | 22.0 | 0.23 |
| 5 | 21.9 | 32.2 | 25.0 | 0.20 |
| CE 1 | 20.9 | 31.6 | 59.0 | 0.085 |

The above data shows that absorbent composites prepared using the chemically stiffened cellulosic fibers provide Acquisition Times and Acquisition Rates that are significantly lower than those provided by absorbent composites that do not include any of the chemically stiffened cellulosic fibers. In addition, the tabulated values show that absorbent composites 1–3, containing chemically stiffened cellulosic fibers, provide Fluid Retentions that are significantly higher than absorbent composites that do not contain any chemically stiffened cellulosic fibers. This is surprising since the absorbent composites 1–3 contained less AGM material than the composites 4–5 and CE1, and Fluid Retention is expected to increase with an increase in AGM concentration.

Laminates are formed from the composites and tested for absorption Capacity Under Pressure, Fluid Retention, and Acquisition Time. The laminates are formed by air-laying about 7 grams of a single composite material onto a pre-weighed 5 cm×20 cm layer of diaper standard tissue (basis weight 0.063–0.070 oz/sq. foot (19.4–21.3 g/m$^2$)), and covering the composite with another pre-weighed 5 cm×20 cm layer of diaper standard tissue (the actual amount of composite in grams, $W_i$, is measured). The composite is substantially uniformly air laid on the lower tissue layer and the tissue layer edges are registered.

Absorption Capacity Under Pressure of Laminates

Absorption Capacity Under Pressure of the laminate is determined as follows. A 5 cm×7 cm sample of the laminate is placed in the flat, unfolded configuration in a container having a sieve positioned at the bottom. A suitable weight is placed on top of the laminate to create a pressure of 0.25 psi over the entire area of the laminate. The container and its contents are weighed and placed on a filter plate in a Petri-dish which is filled with sheep's blood at room temperature (20°–25° C.), such that the sieve comes slightly into contact with the blood. After one hour the laminate is removed from the container. The amount of blood which is absorbed by the laminate is measured by weighing back the container.

The Absorption Capacity Under Pressure (ACUP) of the laminate, in grams sheep's blood per gram of composite, is then calculated as follows:

$$ACUP=(W_t-W_i)+W_{ac}$$

where $W_i$ is the amount of blood absorbed by laminate, $W_t$ is the amount of blood absorbed by the tissue, and $W_{ac}$ is the dry weight of the absorbent composite in the laminate, namely 7 grams.

The amount of the blood absorbed by the tissue is calculated as follows:

(area of tissue in laminate) × (basis weight of the tissue) × (the absorption capacity under pressure of the tissue for sheep's blood, which is 3 grams sheep's blood/gram tissue) × 2

If necessary, the absorption capacity under pressure of the tissue is determined in the same manner of the laminate using calculations readily understood by the skilled artisan in light of the calculations described in reference to the absorbent composites.

The Acquisition Time, Absorption Capacity, and Fluid Retention of the laminates are determined in the manner described in reference to the absorbent composites, except that a sample of the laminate is substituted for the absorbent composite. The laminate sample to be tested weighs the same as noted for the absorbent composite.

The Absorption Capacity Under Pressure, Acquisition Time, and Fluid Retention of the Laminates containing Composites 1–5 and Comparative Example Composite 1 are shown in Table III.

TABLE III

| Example No. | Absorption Capacity Under Pressure, g/g | Acquisition Time, seconds | Fluid Retention, g/g |
|---|---|---|---|
| 1 | 33.2 | 19 | 23.3 |
| 2 | 35.8 | 19.5 | 23.4 |
| 3 | 42.2 | 18 | 28.1 |
| 4 | 34.4 | 22 | 21.1 |
| 5 | 32.2 | 25 | 21.9 |
| CE 1 | 35.1 | 58 | 21.6 |

The tabulated values show that absorbent composites containing chemically stiffened cellulosic fibers provide laminates having Acquisition Times that are significantly lower than the laminates containing absorbent composites that do not contain the chemically stiffened cellulosic fibers. The relatively high Acquisition Time for the laminate containing the Comparative Example Composite 1 indicates that gel blocking is occurring to a significantly greater extent than in the other laminates. In addition, the tabulated values show that absorbent composites 1–3, containing chemically stiffened cellulosic fibers, provide laminates having Fluid Retentions that are significantly higher than the laminates containing absorbent composites that do not contain the chemically stiffened cellulosic fibers. This is surprising since the absorbent composites 1–3 contained less AGM material than the composites 4–5 and CE1, and Fluid Retention is expected to increase with an increase in AGM concentration.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making an absorbent composite comprising particles of polymeric, absorbent gelling material, cellulosic fibers being wrapped around and adhered to said particles by a bonding agent, and crimped, synthetic fibers being attached to said particles of polymeric, absorbent gelling material and said chemically stiffened, cellulosic fibers, the method comprising the steps of:

(a) providing particles of polymeric, absorbent gelling material, chemically stiffened, cellulosic fibers and crimped, synthetic fibers;

(b) applying a bonding agent in liquid form onto said chemically stiffened, cellulosic fibers and said crimped, synthetic fibers to form treated fibers thereof;

(c) physically associating said particles of polymeric, absorbent gelling material and said chemically stiffened, cellulosic fibers and said crimped, synthetic fibers while said bonding agent is in liquid form, said particles being in substantially individual form, such that said chemically stiffened, cellulosic fibers and said crimped, synthetic fibers wrap around said particles; and (d) adhering said particles to said chemically stiffened, cellulosic fibers and said crimped, synthetic fibers by said bonding agent.

* * * * *